US007091201B2

(12) United States Patent
Weller et al.

(10) Patent No.: US 7,091,201 B2
(45) Date of Patent: Aug. 15, 2006

(54) ARYLALKANE-SULFONAMIDES HAVING ENDOTHELIN-ANTAGONIST ACTIVITY

(75) Inventors: Thomas Weller, Binningen (CH); Martin Bolli, Allschwil (CH); Christoph Boss, Allschwil (CH); Martine Clozel, Saint-Louis (FR); Walter Fischli, Allschwil (CH)

(73) Assignee: Actelion Pharmaceuticals Ltd., (CH)

( * ) Notice: Subject to any disclaimer, the term of this patent is extended or adjusted under 35 U.S.C. 154(b) by 447 days.

(21) Appl. No.: 10/381,568

(22) PCT Filed: Aug. 28, 2001

(86) PCT No.: PCT/EP01/09894

§ 371 (c)(1),
(2), (4) Date: Mar. 25, 2003

(87) PCT Pub. No.: WO02/24665

PCT Pub. Date: Mar. 28, 2002

(65) Prior Publication Data

US 2004/0102464 A1 May 27, 2004

(30) Foreign Application Priority Data

Sep. 25, 2000 (WO) ...................... PCT/EP00/09327

(51) Int. Cl.
*C07D 239/46* (2006.01)
*A61K 31/505* (2006.01)
(52) U.S. Cl. .............................. 514/235.8; 514/255.05; 514/256; 514/272; 514/273; 544/123; 544/296; 544/319
(58) Field of Classification Search ................ 544/296, 544/319, 123; 514/235.8, 255.05, 256, 272, 514/273
See application file for complete search history.

(56) References Cited

FOREIGN PATENT DOCUMENTS

| EP | 0 633 259 | 1/1995 |
|----|-----------|--------|
| EP | 0 743 307 | 11/1996 |
| EP | 0 882 719 | 12/1998 |
| FR | 1 549 494 | 10/1967 |
| WO | WO 98/57938 | 12/1998 |

OTHER PUBLICATIONS

Simone, Oncology: Introduction, Cecil Textbook of Medicine, 20th Edition, vol. 1, pp. 1004-1010, 1996.*
Layzer, Degenerative Diseases o the Nervous System, Cecil Textbook of Medicine, 20th Edition, vol. 2, pp. 2050-2057; 1996.*
Damasio, Alzheimer's Disease and related Dementias, Cecil Textbook of Medicine, 20th Edition, vol. 2, pp. 1992-1996, 1996.*
Arai et al., "Cloning and expression of a cDNA encoding an endothelin receptor". Nature. Dec. 20-27, 1990; 348(6303):730-732.

Breu et al., "In vitro characterization of Ro 46-2005, a novel synthetic non-peptide endothelin antagonist of ETA and ETB receptors". FEBS Lett. Nov. 15, 1993;334(2):210-214.
Brown et al., "Isomerizations Akin to the Dimroth Rearrangement .III The Conversion of Simple s-Triazolo[4,3-α]pyrimidines into Their[1,5-α]Isomers". Aust. J. Chem. 1977, 30:2515-2525.
Brown et al., "Pyrimidne Reactions". Aust. J. Chem. 1964, 17:794-802.
Crosby et al., "n-Butyl 5-Chloro-2-pyrimidoxyacetate-A Plant Growth Regulator Analog". J. Org. Chem. 1960, 25:1916-1919.
Gohring et al., "Development of a process to prepare 2-cyanopyrimidine on commercial scale". Chimia, 1996, 50:538-543.
Jacobsen et al., "Phenylation of pyrimidinones using diphenyliodonium salts". J. Chem. Soc. Perkin Trans. 1999, 1:3265-3268.
Kempf et al., "Symmetry-based inhibitors of HIV protease. Structure-activity studies of acylated 2,4-diamino-1,5-diphenyl-3-hydroxypentane and 2,5-diamino-1,6-diphenylhexane-3,4-diol". J Med Chem. Feb. 5, 1993;36(3):320-330.
Kohara et al., "Synthesis and angiotensin II receptor antagonistic activities of benzimidazole derivatives bearing acidic heterocycles as novel tetrazole bioisosteres". J Med Chem. Dec. 20, 1996;39(26):5228-5235.
Koppel et al., "Pyrimidines. X. (Antibiotics. II) Synthesis of Bacimethrin, 2-Methoxy Analog of Thiamine, and Related Alkoxypyrimidines". J. Org. Chem. 1962, 27:3614-3617.
Maggiali et al. "Effetti Anti H1-Istaminici E Antimuscarinici Di Composti 2-E E-[Benzil-(2-Dimetilaminoetil)Amino]Pirimidinici". Il Farmaco 1988, 43:277-292 (in Italian with English Summary).
March, J. Advanced Organic Chemistry. 4th Ed., 1994, p. 499.
McMillen et al., "Endothelins: polyfunctional cytokines". J Am Coll Surg. May 1995;180(5):621-637.
Neidhart et al., "Discovery of RO 48-5695: A potent mixed endothelin receptor antagonist optimized from Bosentan. Bioorg". Med. Chem. Lett. 1997, 7:2223-2228.
Neidhart et al., "The discovery of nonpeptide endothelin receptor antagonists. Progression towards Bosentan". Chimia 1996, 50:519-524.
Nugent et al., "Pyrimidine thioethers: a novel class of HIV-1 reverse transcriptase inhibitors with activity against BHAP-resistant HIV". J Med Chem. Sep. 24, 1998;41(20):3793-3803.
Ogawa et al., Molecular cloning of a non-isopeptide-selective human endothelin receptor. Biochem Biophys Res Commun. Jul. 15, 1991;178(1):248-255.

(Continued)

Primary Examiner—Deepak Rao
(74) Attorney, Agent, or Firm—Gibbons, Del Deo, Dolan, Griffinger & Vecchione

(57) ABSTRACT

The invention relates to novel aryl-alkane-sulfonamides and their use as active ingredients in the preparation of pharmaceutical compositions. The invention also concerns related aspects including processes for the preparation of the compounds, pharmaceutical compositions containing one or more of those compounds and especially their use as endothelin receptor antagonists.

14 Claims, No Drawings

OTHER PUBLICATIONS

Ohlstein et al., Drug. Dev. Res. 1993, 29:108.

Rubanyi et al., "Endothelins: molecular biology, biochemistry, pharmacology, physiology, and pathophysiology". Pharmacol Rev. Sep. 1994;46(3):325-415. Review.

Sakurai et al., "Cloning of a cDNA encoding a non-isopeptide-selective subtype of the endothelin receptor". Nature. Dec. 20-27, 1990;348(6303):732-735.

Sumner et al., Endothelin ETA and ETB receptors mediate vascular smooth muscle contraction. Br J Pharmacol. Nov. 1992;107(3):858-860.

Ueda et al., "Nuleosides. XVII. Pyrimidinyl Amino Acids". J. Med. Chem. 1963, 6:697-701.

Yamanaka et al., "Preparation of Novel β-Trifluoromethyl vinamidinium Salt and Its Synthetic Application to Trifluoromethylated Heterocycles". Tetrahedron Lett. 1996, 37:1829-1832.

Yanagisawa et al., "A novel potent vasoconstrictor peptide produced by vascular endothelial cells". Nature. Mar. 31, 1988;332(6163):411-415.

Zhong et al., "Active-Site-Directed Modification of Subtilisin". J. Am. Chem. Soc. 1991, 113:2259-2263.

* cited by examiner

ARYLALKANE-SULFONAMIDES HAVING ENDOTHELIN-ANTAGONIST ACTIVITY

The present invention relates to novel arylalkane-sulfonamides of the general formula I and their use as active ingredients in the preparation of pharmaceutical compositions. The invention also concerns related aspects including processes for the preparation of the compounds, pharmaceutical compositions containing one or more compounds of the general formula I and especially their use as endothelin receptor antagonists.

Endothelins (ET-1, ET-2, and ET-3) are 21-amino acid peptides produced and active in almost all tissues (Yanagisawa M et al.: Nature (1988) 332:411). Endothelins are potent vasoconstrictors and important mediators of cardiac, renal, endocrine and immune functions (McMillen M A et al.: J Am Coll Surg (1995) 180:621). They participate in bronchoconstriction and regulate neurotransmitter release, activation of inflammatory cells, fibrosis, cell proliferation and cell differentiation (Rubanyi G M et al.: Pharmacol Rev (1994) 46:328).

Two endothelin receptors have been cloned and characterized in mammals ($ET_A$, $ET_B$) (Arai H et al.: Nature (1990) 348:730; Sakurai T et al.: Nature (1990) 348:732). The $ET_A$ receptor is characterized by higher affinity for ET-1 and ET-2 than for ET-3. It is predominant in vascular smooth muscle cells and mediates vasoconstricting and proliferative responses (Ohlstein E H et al.: Drug Dev Res (1993) 29:108). In contrast, the $ET_B$ receptor has equivalent affinity for the 3 endothelin isopeptides and binds the linear form of endothelin, tetra-ala-endothelin, and sarafotoxin S6C (Ogawa Y et al.: BBRC (1991) 178:248). This receptor is located in the vascular endothelium and smooth muscles, and is also particularly abundant in lung and brain. The $ET_B$ receptor from endothelial cells mediates transient vasodilator responses to ET-1 and ET-3 through the release of nitric oxide and/or prostacyclin whereas the $ET_B$ receptor from smooth muscle cells exerts vasoconstricting actions (Sumner M J et al.: Brit J Pharmacol (1992) 107:858). $ET_A$ and $ET_B$ receptors are highly similar in structure and belong to the superfamily of G-protein coupled receptors.

A pathophysiological role has been suggested for ET-1 in view of its increased plasma and tissue levels in several disease states such as hypertension, sepsis, atherosclerosis, acute myocardial infarction, congestive heart failure, renal failure, migraine and asthma. As a consequence, endothelin receptor antagonists have been studied extensively as potential therapeutic agents. Endothelin receptor antagonists have demonstrated preclinical and/or clinical efficacy in various diseases such as cerebral vasospasm following subarachnoid hemorrhage, heart failure, pulmonary and systemic hypertension, neurogenic inflammation, renal failure and myocardial infarction.

Today, no endothelin receptor antagonist is marketed yet, several are in clinical trials. However, these molecules possess a number of weaknesses such as complex synthesis, low solubility, high molecular weight, poor pharmacokinetics, or safety problems (e.g. liver enzyme increases).

The inhibitory activity of the compounds of general formula I on endothelin receptors can be demonstrated using the test procedures described hereinafter:

For the evaluation of the potency and efficacy of the compounds of the general formula I the following tests were used:

1) Inhibition of Endothelin Binding to Membranes from CHO Cells Carrying Human ET Receptors:

For competition binding studies, membranes of CHO cells expressing human recombinant $ET_A$ or $ET_B$ receptors were used. Microsomal membranes from recombinant CHO cells were prepared and the binding assay made as previously described (Breu V., et al, FEBS Lett 1993; 334:210).

The assay was performed in 200 uL 50 mM Tris/HCl buffer, pH 7.4, including 25 mM $MnCl_2$, 1 mM EDTA and 0.5% (w/v) BSA in polypropylene microtiter plates. Membranes containing 0.5 ug protein were incubated for 2 h at 20° C. with 8 pM [$^{125}$I]ET-1 (4000 cpm) and increasing concentrations of unlabelled antagonists. Maximum and minimum binding were estimated in samples without and with 100 nM ET-1, respectively. After 2 h, the membranes were filtered on filterplates containing GF/C filters (Unifilterplates from Can berra Packard S. A. Zürich, Switzerland). To each well, 50 uL of scintillation cocktail was added (MicroScint 20, Can berra Packard S. A. Zürich, Switzerland) and the filter plates counted in a microplate counter (TopCount, Can berra Packard S. A. Zürich, Switzerland).

All the test compounds were dissolved, diluted and added in DMSO. The assay was run in the presence of 2.5% DMSO which was found not to interfere significantly with the binding. $IC_{50}$ was calculated as the concentration of antagonist inhibiting 50% of the specific binding of ET-1. For reference compounds, the following $IC_{50}$ values were found: $ET_A$ cells: 0.075 nM (n=8) for ET-1 and 118 nM (n=8) for ET-3; $ET_B$ cells: 0.067 nM (n=8) for ET-1 and 0.092 nM (n=3) for ET-3.

The $IC_{50}$ values obtained with compounds of general formula I are given in Table 1.

TABLE 1

| Compound of Example | $IC_{50}$ $ET_A$ [nM] | $IC_{50}$ $ET_B$ [nM] |
|---|---|---|
| Example 1 | 27 | 6650 |
| Example 2 | 20 | 899 |
| Example 5 | 3 | 323 |
| Example 7 | 4 | 3310 |
| Example 10 | 9 | 2410 |
| Example 13 | 4 | 3680 |
| Example 14 | 6 | 2230 |
| Example 19 | 3 | 1930 |
| Example 29 | 10 | 406 |
| Example 39 | 3 | 261 |
| Example 46 | 7 | 2360 |
| Example 47 | 24 | 2720 |
| Example 49 | 4 | 2490 |
| Example 52 | 5 | 1770 |
| Example 61 | 10 | 1140 |
| Example 71 | 115 | >10000 |
| Example 81 | 24 | 824 |

2) Inhibition of Endothelin-Induced Contractions on Isolated Rat Aortic Rings ($ET_A$ Receptors) and Rat Tracheal Rings ($ET_B$ Receptors):

The functional inhibitory potency of the endothelin antagonists was assessed by their inhibition of the contraction induced by endothelin-1 on rat aortic rings ($ET_A$ receptors) and of the contraction induced by sarafotoxin S6c on rat tracheal rings ($ET_B$ receptors). Adult Wistar rats were anesthetized and exsanguinated. The thoracic aorta or trachea were excised, dissected and cut in 3–5 mm rings. The endothelium/epithelium was removed by gentle rubbing of the intimal surface. Each ring was suspended in a 10 ml isolated organ bath filled with Krebs-Henseleit solution (in mM; NaCl 115, KCl 4.7, $MgSO_4$ 1.2, $KH_2PO_4$ 1.5, $NaHCO_3$ 25, $CaCl_2$ 2.5, glucose 10) kept at 37° C. and gassed with 95% $O_2$ and 5% CO. The rings were connected to force transducers and isometric tension was recorded (EMKA Technologies SA, Paris, France). The rings were stretched to a resting tension of 3 g (aorta) or 2 g (trachea). Cumulative doses of ET-1 (aorta) or sarafotoxin S6c (trachea) were added after a 10 min incubation with the test compound or its vehicle. The functional inhibitory potency of the test compound was assessed by calculating the concentration ratio, i.e. the shift to the right of the $EC_{50}$ induced by different concentrations of test compound. $EC_{50}$ is the concentration of endothelin needed to get a half-maximal contraction, $pA_2$ is the negative logarithm of the antagonist concentration which induces a two-fold shift in the $EC_{50}$ value.

The $pA_2$ values obtained with compounds of formula I are given in Table 2.

TABLE 2

| Compound of Example | pA$_2$ (aortic rings) | pA$_2$ (trachea) |
|---|---|---|
| Example 5 | 8.38 | 7.02 |
| Example 7 | 8.83 | 7.07 |
| Example 8 | 7.43 | — |
| Example 34 | 7.67 | — |
| Exampl 61 | 7.83 | 7.07 |
| Example 75 | 7.76 | — |

Because of their ability to inhibit the endothelin binding, the described compounds can be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension and pulmonary hypertension. They can also be used for atherosclerosis, prevention of restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain as well as other diseases presently known to be related to endothelin.

The compounds can be administered orally, rectally, parenterally, e.g. by intravenous, intramuscular, subcutaneous, intrathecal or transdermal administration or sublingually or as ophthalmic preparation or administered as aerosol. Examples of applications are capsules, tablets, orally administered suspensions or solutions, suppositories, injections, eye-drops, ointments or aerosols/nebulizers.

Preferred applications are intravenous, intramuscular, or oral administrations as well as eye drops. The dosage used depends upon the type of the specific active ingredient, the age and the requirements of the patient and the kind of application. Generally, dosages of 0.1–50 mg/kg body weight per day are considered. The preparations with compounds can contain inert or as well pharmacodynamically active excipients. Tablets or granules, for example, could contain a number of binding agents, filling excipients, carrier substances or diluents.

The present invention relates to arylethene-sulfonamides of the general formula I,

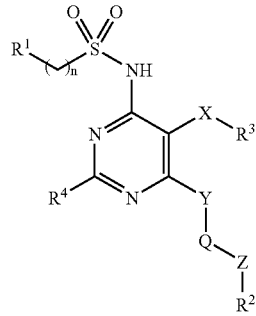

General Formula I wherein
$R^1$ and $R^2$ represent aryl; heteroaryl;
$R^3$ represents phenyl; mono-, di- or tri-substituted phenyl substituted with lower alkyl, lower alkenyl, lower alkynyl, phenyl, lower alkoxy, amino, lower alkylamino, amino-lower alkyl, trifluoromethyl, trifluoromethoxy, halogen, lower alkylthio, hydroxy, hydroxy-lower alkyl, cyano, carboxyl, lower alkanoyl, formyl; benzofuranyl; aryl; heteroaryl;
$R^4$ represents hydrogen; halogen; trifluoromethyl; lower alkyl; lower alkyl-amino; lower alkoxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkylthio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; cycloalkyl-sulfinyl;
X represents oxygen; sulfur; NH; $CH_2$ or a bond;
Y represents oxygen; sulfur or —NH—;
Z represents oxygen; sulfur, —NH— or a bond;
Q represents —$(CH_2)_k$—; —$(CH_2)_m$—C≡C—$(CH_2)_p$—, in case p represents 0(zero), Z represents a bond; —$CH_2$-cyclopropylen-$CH_2$—;
k represents the numbers 2, 3; 4, 5, or 6;
m represents the numbers 1, 2, or 3;
p represents the numbers 0, 1, 2 or 3;
n represents the numbers 1, 2, or 3;
and pure diastereomers, mixtures of diastereomers, diastereomeric racemates, mixtures of diastereomeric racemates and the meso-forms and pharmaceutically acceptable salts thereof.

In the definitions of the general formula I—if not otherwise stated—the expression lower alkyl or lower alkoxy means straight and branched chain groups with one to seven carbon atoms, preferably 1 to 4 carbon atoms. Examples of lower alkyl and lower alkoxy groups are methyl, ethyl, n-propyl, isopropyl, n-butyl, isobutyl, sec.-butyl, tert.-butyl, pentyl, hexyl, heptyl, methoxy, ethoxy, propoxy, n-butoxy, iso-butoxy, sec.-butoxy and tert.-butoxy. Lower alkylendioxy-groups are preferably methylene-dioxy, ethylene-dioxy, propylene-dioxy and butylen-dioxy groups. Examples of lower alkanoyl-groups are acetyl, propanoyl and butanoyl. Lower alkenylen means e.g.vinylen, propenylen and butenylen. Lower alkenyl and lower alkynyl means groups like ethylene, propylen, butylen, 2-methyl-propenyl, and ethinylen, propinylen, butinylen, pentinylen, 2-methyl-pentinylen etc. Lower alkenyloxy means allyloxy, vinyloxy, propenyloxy and the like. The expression cycloalkyl means a saturated cyclic hydrocarbon ring with 3 to 7 carbon atoms, e.g. cyclopropyl, cyclobutyl, cyclopentyl, cyclohexyl and cycloheptyl, which may be substituted with lower alkyl, hydroxy-lower alkyl, amino-lower alkyl, lower alkoxy-lower alkyl and lower alkenylen groups. The expression heterocyclyl means saturated or partially unsaturated four, five-, six- or seven-membered rings containing one or two nitrogen, oxygen or sulfur atoms which may be the same or different and which rings may be adequatly substituted with lower alkyl, amino, nitro, hydroxy, lower alkoxy, e.g. piperidinyl, morpholinyl, thiomorpholinyl, piperazinyl, tetrahydropyranyl, dihydropyranyl, 1,4-dioxanyl, pyrrolidinyl, tetrahydrofuranyl, dihydropyrrolyl, dihydroimidazolyl, dihydropyrazolyl, pyrazolidinyl, 5-oxo-1,2,4-oxadiazolyl, 5-oxo-1,2,4-thiadiazolyl, 5-thioxo-1,2,4-oxadiazolyl, 2-oxo-1,2,3,5-oxathiadiazolyl etc. (e.g.[7]) and substituted derivatives of such rings with substituents as outlined above. The expression heteroaryl means six-membered aromatic rings containing one to four nitrogen atoms, benzofused six-membered aromatic rings containing one to three nitrogen atoms, five-membered aromatic rings containing one oxygen or one nitrogen or one sulfur atom, benzo-fused five-membered aromatic rings containing one oxygen or one nitrogen or one sulfur atom, five membered aromatic rings containing an oxygen and nitrogen atom and benzo fused derivatives thereof, five membered aromatic rings containing a sulfur and a nitrogen atom and benzo fused derivatives thereof, five-membered aromatic rings containing two nitrogen atoms and benzo fused derivatives thereof, five membered aromatic rings containing three nitrogen atoms and benzo fused derivatives thereof or the tetrazolyl ring; e.g. furanyl, thienyl, pyrrolyl, pyridinyl, pyrimidinyl, indolyl, quinolinyl, isoquinolinyl, imidazolyl, triazinyl, thiazinyl, thiazolyl, isothiazolyl, pyridazinyl, oxazolyl, isoxazolyl, etc. whereby such rings may be substituted with lower alkyl, lower alkenyl, amino, amino-lower alkyl, halogen, hydroxy, lower alkoxy, trifluoromethoxy, trifluoromethyl, carboxyl, carboxamidyl, thioamidyl, amidinyl, lower alkoxy, cyano, hydroxy-lower alkyl, lower alkoxy-lower alkyl or another heteroaryl- (preferrably tetrazolyl) or heterocyclyl-ring (preferrably 5-oxo-1,2,4-oxadiazolyl, 5-oxo-1,2,4-triazolyl, 5-oxo-1,2,4-thiadiazolyl, 5-thioxo-1,2,4-oxadiazolyl or 2-oxo-1,2,3,5-oxathiadiazolyl (e.g. [7])). The expression aryl represents unsubstituted as well as mono-, di- or tri-substituted aromatic rings with 6 to 10 carbon atoms like phenyl or naphthyl rings which may be substituted with aryl, halogen, hydroxy, lower alkyl, lower alkenyl, lower alkynyl, lower alkoxy, lower alkenyloxy, lower alkynyl-lower alkyloxy, lower alkenylen, lower alkylenoxy, lower alkylenoxy or lower alkylendioxy forming with the phenyl ring a five- or six-membered ring, hydroxy-lower alkyl, hydroxy-lower alkenyl, hydroxy-lower alkyl-lower alkynyl, lower alkoxy-lower alkyl, lower alkoxy-lower alkoxy, trifluoromethyl, trifluoromethoxy, cycloalkyl, hydroxy-cycloalkyl, heterocyclyl, heteroaryl.

It is understood that the substituents outlined relative to the expressions cycloalkyl, heterocyclyl, heteroraryl and aryl have been omitted in the definitions of the general formulae I to V in claims 1 to 11 for clarity reasons but the definitions in formulae I to V and in claims 1 to 11 should be read as if they are included therein.

Especially preferred compounds are compounds of general formula I wherein $R^3$ represents phenyl or mono-substituted phenyl substituted with lower alkoxy, especially methoxy and X represents oxygen.

A second group of especially preferred compounds of general formula I are the compounds wherein $R^3$ represents phenyl or mono-substituted phenyl substituted with lower alkoxy, especially methoxy, and wherein X, Y and Z represent oxygen.

A third group of especially preferred compounds of general formula I are the compounds wherein $R^3$ represents phenyl or mono-substituted phenyl substituted with lower alkoxy, especially methoxy, and wherein X, Y and Z represent oxygen and Q represents —$(CH_2)_k$— with k=2 or 3.

A fourth group of especially preferred compounds of general formula I are the compounds wherein $R^2$ represents heteroaryl, $R^3$ represents phenyl or mono-substituted phenyl substituted with lower alkoxy, especially methoxy, X, Y and Z represent oxygen and Q represents —$(CH_2)_k$— with k=2 or 3.

A fifth group of especially preferred compounds of general formula I are the compounds wherein $R^2$ represents heteroaryl, $R^3$ represents phenyl or mono-substituted phenyl substituted with halogen, lower alkyl, lower alkenyl, methoxy, amino, lower alkyl-amino, lower alkyl-thio, hydroxy, hydroxymethyl and lower alkanoyl; X, Y and Z represent oxygen, Q represents —$(CH_2)_2$—.

Another group of preferred compounds are compounds of formula II

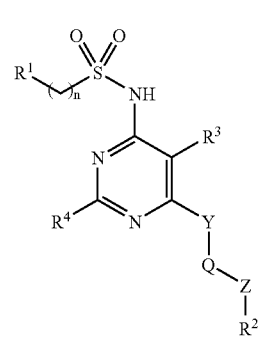

Formula II wherein $R^1$, $R^2$, $R^3$, $R^4$, Y, Q, Z, and n are as defined in general formula I above, and pharmaceutically acceptable salts of compounds of formula II.

Also preferred are compounds of formula III

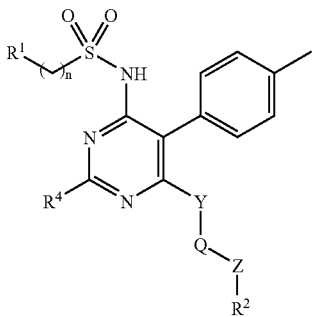

Formula III wherein $R^1$, $R^2$, $R^4$, Y, Q and Z and n are as defined in general formula I above, and pharmaceutically acceptable salts of compounds of formula III.

Also preferred are compounds of formula IV

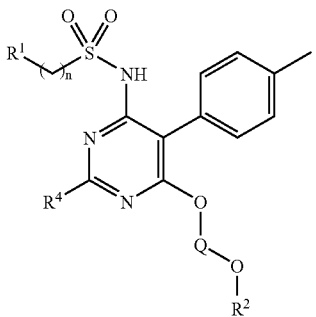

Formula IV wherein $R^1$, $R^2$, $R^4$, Q, and n are as defined in general formula I above, and pharmaceutically acceptable salts of compounds of formula IV.

Another especially preferred group of compounds are compounds of formula V

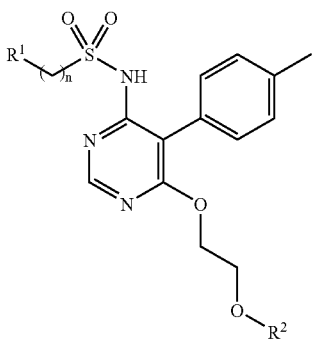

Formula V wherein $R^1$ and $R^2$ are as defined in general formula I above, and pharmaceutically acceptable salts thereof.

Especially preferred compounds among the group of compounds of formula V are those wherein $R^2$ represents heteroaryl.

The expression pharmaceutically acceptable salts encompasses either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methylsulfonic acid, p-toluolsulfonic acid and the like or in case the compound of formula I is acidic in nature with an inorganic base like an alkali or earth alkali base, e.g. sodium hydroxide, potassium hydroxide, calcium hydroxide etc.

The compounds of the general formula I might have one or more asymmetric carbon atoms and may be prepared in form of optically pure enantiomers or diastereomers, mixtures of enantiomers or diastereomers, diastereomeric racemates, mixtures of diastereomeric racemates and also in the meso-form. The present invention encompasses all these forms. Mixtures may be separated in a manner known per se, i.e. by column chromatography, thin layer chromatography, HPLC, crystallization etc.

Because of their ability to inhibit the endothelin binding, the described compounds of the general formula I and their pharmaceutically acceptable salts may be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension and pulmonary hypertension. They can also be used for atherosclerosis, prevention of restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain, as well as other diseases presently known to be related to endothelin.

These compositions may be administered in enteral or oral form e.g. as tablets, dragees, gelatine capsules, emulsions, solutions or suspensions, in nasal form like sprays or rectically in form of suppositories. These compounds may also be administered in intramuscular, parenteral or intravenous form, e.g. in form of injectable solutions.

These pharmaceutical compositions may contain the compounds of formula I as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols etc. may be used. For the preparation of solutions and sirups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, anti-oxidants etc.

The compounds of formula I may also be used in combination with one or more other therapeutically useful substances e.g. α- and β-blockers like phentolamine, phenoxybenzamine, atenolol, propranolol, timolol, metoprolol, carteolol etc.; Vasodilators like hydralazine, minoxidil, diazoxide, flosequinan etc.; Calcium-antagonists like diltiazem, nicardipine, nimodipine, verapamil, nifedipine etc.; ACE-inhibitors like cilazapril, captopril, enalapril, lisinopril etc.; Potassium activators like pinacidil etc.; Angiotensin II antagonists; Diuretics like hydrochlorothiazide, chlorothiazide, acetolamide, bumetanide, furosemide, metolazone, chlortalidone etc.; Sympatholitics like methyldopa, clonidine, guanabenz, reserpine etc.; and other therapeutics which serve to treat high blood pressure or any cardiac disorders.

The dosage may vary within wide limits but should be adapted to the specific situation. In general the dosage given daily in oral form should be between about 3 mg and about 3 g, preferably between about 10 mg and about 1 g, especially preferred between 5 mg and 300 mg, per adult with a body weight of about 70 kg. The dosage should be administered preferably in 1 to 3 doses per day which are of equal weight. As usual children should receive lower doses which are adapted to body weight and age.

Compounds of the general formula I of the present invention can be prepared according to the general sequence of reactions outlined below. For simplicity and clarity reasons sometimes only parts of the synthetic possibilities which lead to compounds of general formula I are described. The literature references given in brackets [ ] are set forth at the end of this paragraph.

Possibility A:

The desired compounds of general formula I can be prepared by reacting a compound of the formula 1:

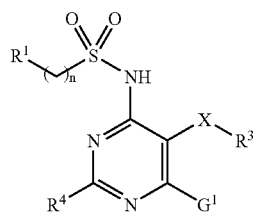

Formula 1 wherein $G^1$ is a reactive residue, preferentially a chlorine atom, and the other symbols are as defined in general formula I above, with a compound of the formula 2:

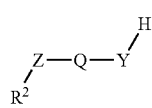

Formula 2 wherein the symbols are the same as defined in general formula I above, or a salt thereof.

Possibility B:

The compounds of general formula I may also be prepared by reacting a compound of formula 3:

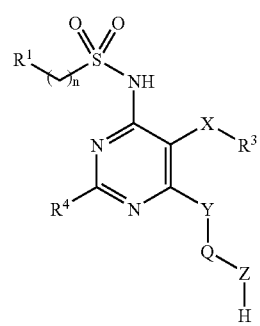

Formula 3 wherein the symbols are the same as defined in general formula I above, or a salt thereof, with a compound of the formula 4

Formula 4 wherein $G^2$ is a reactive residue, such as a halogen atom, and $R^2$ is as defined in general formula I above.

Possibility C:

The compounds of general formula I may also be prepared by reacting a compound of the formula 5:

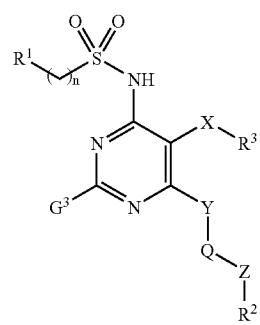

Formula 5

Wherein $G^3$ is a lower alkylsulfonyl group or a phenylsulfonyl group or a halogen atom, and the other symbols are the same as described in general formula I above, or a salt thereof, with a compound of the formula 6:

Formula 6 wherein $R^4$ is as defined in general formula I above, or a salt thereof.

For possibilities A to C see also [5].

Scheme 1: Preparation of the precursors 1 and 3, with X, Y and Z representing oxygen:

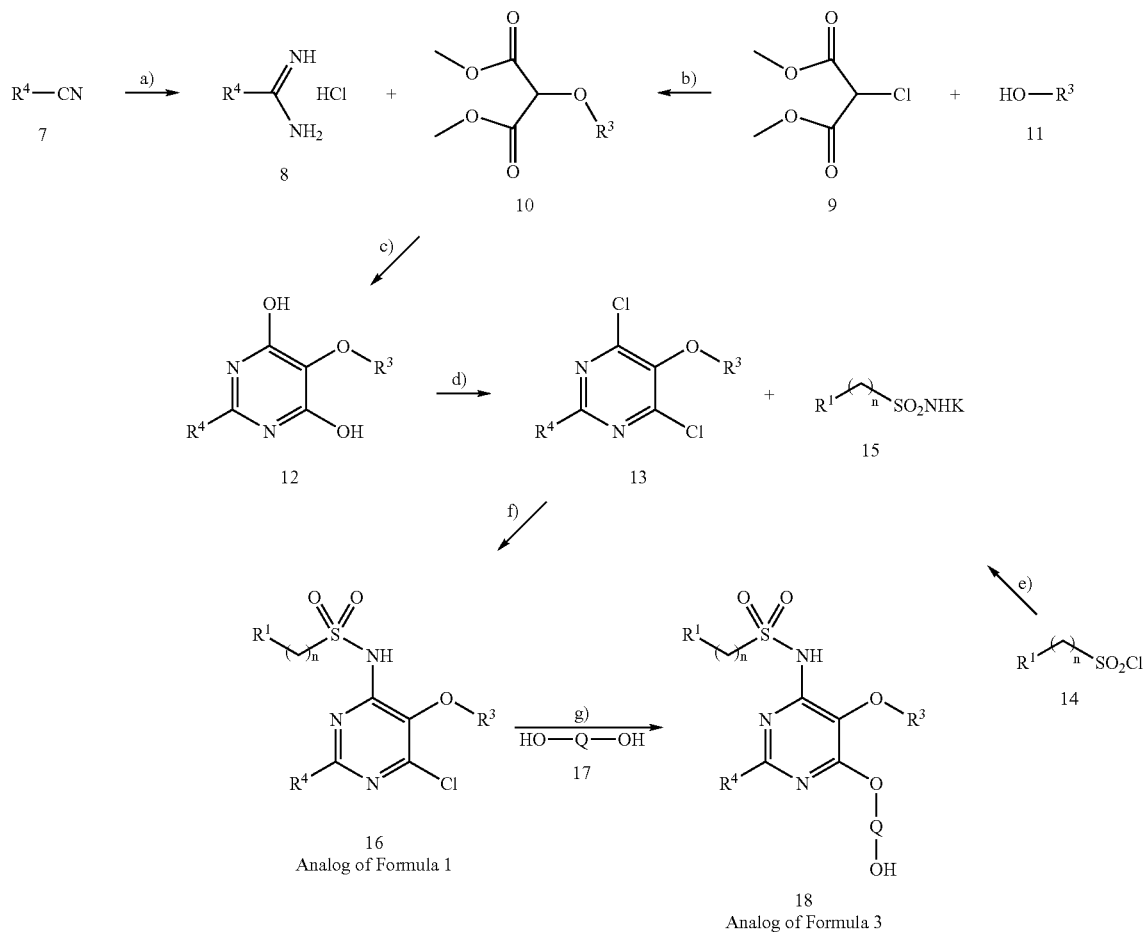

a) NaOMe, MeOH then NH$_4$Cl or LiN(Si(CH$_3$)$_3$)$_2$ then HCl/i-PrOH; b) K$_2$CO$_3$, acetone; c) NaOMe, MeOH; d) POCl$_3$; e) NH$_3$/THF then KOtBu, MeOH; f) DMSO; g) NaH, THF, DMF;

The amidines 8 were synthesized applying standard methodology [1] by reaction of the appropriate nitrile 7 either with sodium methylate in methanol followed by addition of ammonium chloride or by reaction with lithium hexamethyldisilazane followed by addition of hydrochloric acid in i-propanol. The 2-substituted malonic esters 10 were prepared according to published procedures [2] by reacting dimethylchloromalonate (9) with the appropriate alcohol 11 in acetone and potassium carbonate as base. The compounds 10 were dissolved in methanol and sodium methylate was added and stirring was continued for about 30 min followed by the addition of an amidine derivative 8. Stirring at ambient temperature was continued for another 8 h. After acidic work up the 4,6-dihydroxypyrimidines 12 could be isolated in yields of 70 to 90% [2]. Compounds 12 or the tautomeric form thereof were transformed into the dichloro derivatives 13 with phosphorus oxychloride in the presence of N,N-dimethylaniline at elevated temperatures (60–120° C.) in yields of 40 to 75% [3]. In some cases better yields were obtained by addition of PCl$_5$ or benzyl-triethylammoniumchloride. The dichlorides 13 were reacted with an excess of the appropriate sulfonamide potassium salt 15 (prepared according to standard methodology from the sulfochlorides 14 (for the preparation of 14 see e.g. [9], [10]) in DMSO at rt to give the pyrimidines 16 in yields of 70 to 90% either after recrystallization from EA/diethylether or chromatography through silica gel with EA/heptane. The pyrimidine derivatives 16 are the key intermediates which can be transformed to the desired final products of general formula I either by applying procedures outlined under Possibility A or they can be transformed to the derivatives 18 by reaction with a di-hydroxy-compound represented by formula 17 in the presence of a base such as sodium hydride in a solvent like THF at rt to 90° C. and can then be transformed to final compounds according to the general formula I by applying procedures outlined under Possibility B above.

For further experimental descriptions see [1], [2], [3], [6].

The synthesis of compounds with X, Y or Z being other groups than oxygen, can be carried out in analogous manners.

Scheme 2: Preparation of the precursor 5, with X, Y and Z representing oxygen:

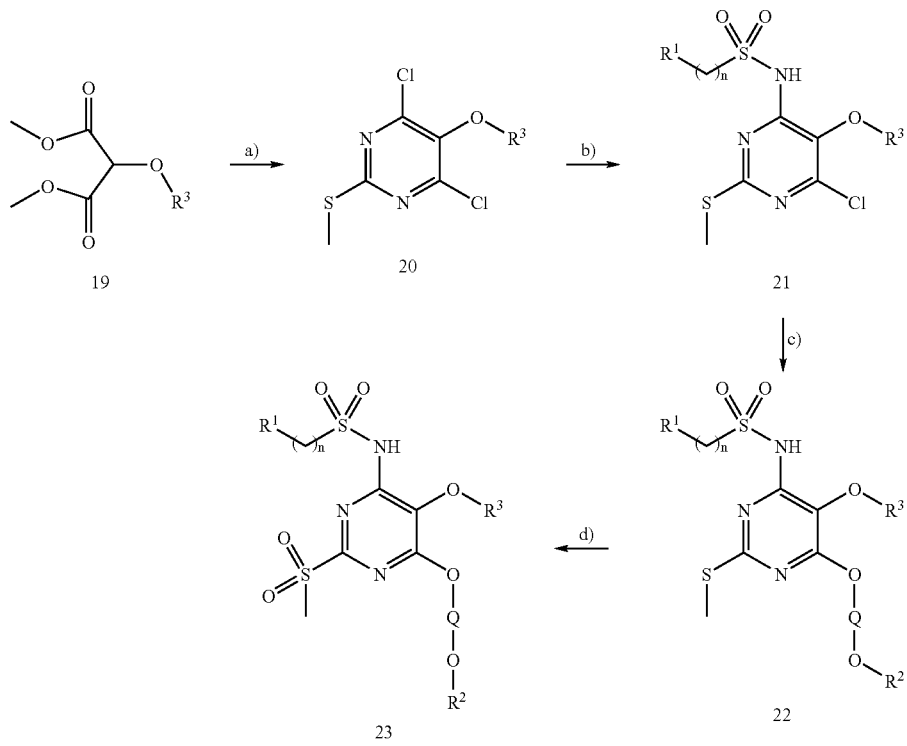

23
Analog of Formula 5 a) i) thiourea, NaOMe, MeOH, rt; ii) CH$_3$I, DMSO rt; iii) POCl$_3$, dimethylaniline, 100–120° C.
b) R$^1$—(CH$_2$)$_n$—SO$_2$—NHK, DMSO, rt; c) R$^2$—O—Q—OH, NaH, THF/DMF, rt or 60–80° C.
or HO—Q—OH, NaH, THF/DMF, rt or 60–80° C. followed by G$^2$—R$^2$, NaH, THF, 60–80° C.; d) MCPBA, DCM, rt.

For further experimental descriptions see [1], [2], [3], [5] [6]. For the substitution of the sulfono-group, see especially [5].

The synthesis of compounds with X, Y or Z being another group than oxygen, can be carried out in analogous procedures.

Scheme 3: Preparation of the precursors for the synthesis of compounds of general formula I wherein X represents a bond [5]:

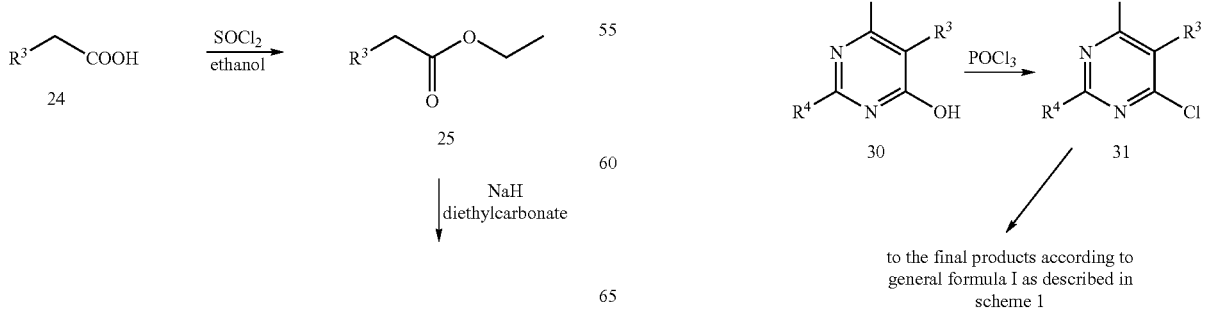

to the final products according to general formula I as described in scheme 1

In the schemes 1 to 3 the symbols represent the same as defined in general formula I above.

[1] W. Göhring, J. Schildknecht, M. Federspiel; *Chimia,* 50 (1996), 538–543.
[2] W. Neidhart, V. Breu, D. Bur, K. Burri, M. Clozel, G. Hirth, M. Müller, H. P. Wessel, H. Ramuz; *Chimia,* 50 (1996), 519–524 and references cited there.
[3] W. Neidhart, V. Breu, K. Burri, M. Clozel, G. Hirth, U. Klinkhammer, T. Giller, H. Ramuz; *Bioorg. Med. Chem. Lett.,* 7 (1997), 2223–2228. R. A. Nugent, S. T. Schlachter, M. J. Murphy, G. J. Cleek, T. J. Poel, D. G. Whishka, D. R. Graber, Y. Yagi, B. J. Keiser, R. A. Olmsted, L. A. Kopta, S. M. Swaney, S. M. Poppe, J. Morris, W. G. Tarpley, R. C. Thomas; *J. Med. Chem.,* 41 (1998), 3793–3803.
[4] J. March; *Advanced Organic Chemistry,* 4th Ed., 1994, p. 499 and references cited there.
[5] EP 0 743 307 A1; EP 0 658 548 B1; EP 0 959 072 A1 (Tanabe Seiyaku)
[6] EP 0 633 259 B1; EP 0 526 708 A1; WO 96/19459 (F. Hoffmann-LaRoche)
[7] for the Synthesis of 5-membered heterocycles see: Y. Kohara et al; *J. Med. Chem.,* 39 (1996), 5228–5235 and references cited there.
[8] EP 0 882 719 A1 (Yamanouchi Pharmaceutical Co., Ltd)
[9] Z. Zhong,J. A. Bibbs, W. Yuan, C.-H. Wong, *J. Am. Chem. Soc.* 113, (1991), 2259–2263
[10] D. J. Kempf, L. Codavoci, X. C. Wang, W. E. Kohlbrenner, N. E. Wideburg, A. Saldivar, S. Vasavanonda, K. C. Marsh, P. Bryant, H. L. Sham, B. E. Green, D. A. Betebenner, J. Erikson, D. W. Norbeck, *J. Med. Chem.* 36 (1993), 320–330

REFERENTIAL EXAMPLES (SYNTHESIS OF PRECURSORS)

| List of abbreviations: | |
|---|---|
| CyHex | cyclohexane |
| DCM | dichloromethane |
| DME | 1,2-dimethoxyethane |
| DMF | dimethylformamide |
| DMSO | dimethylsulfoxide |
| EA | ethyl acetate |
| Hex | hexane |
| HV | high vacuum conditions |
| MCPBA | m-chloroperbenzoic acid |
| min | minutes |
| rt | room temperature |
| THF | tetrahydrofurane |
| sat. | saturated |
| $t_R$ | retention time |

The following referential examples illustrate the invention but do not at all limit the scope thereof.

The following compounds were prepared according to the procedure described above and shown in Schemes 1 to 3. All compounds were characterized by $^1$H-NMR (300 MHz) and occasionally by $^{13}$C-NMR (75 MHz) (Varian Oxford, 300 MHz; chemical shifts are given in ppm relative to the solvent used; multiplicities: s=singlet, d=doublet, t=triplet; m=multiplett, coupling constants J in Hz), by LC-MS (Waters Micromass; ZMD-plafform with ESI-probe with Alliance 2790 HT; Colum: 2×30 mm, Gromsil ODS4, 3μm, 120A; Gradient: 0–100% acetonitril in water, 6 min, with 0.05% formic acid, flow: 0.45 ml/min; $t_R$ is given in min.), by TLC (TLC-plates from Merck, Silica gel 60 $F_{254}$) and occasionally by melting point. All temperatures are stated in ° C.

Referential Example 1

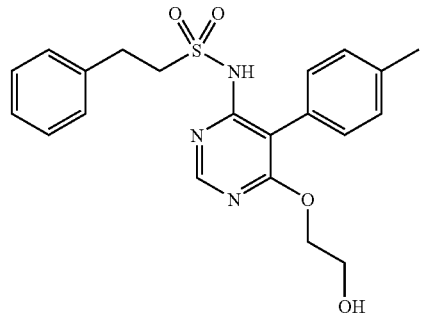

a) Sodium methylate (17 g) was dissolved in methanol (600 ml) at 0° C. 2-p-tolyl-malonic acid diethyl ester (24.5 ml, commercially available from Aldrich), dissolved in 150 ml methanol, was added within 30 min. Stirring was continued for 1 h while slowly warming the mixture to rt. Formamidine hydrochloride (9.9 g, commercially available from Fluka) was added and stirring was continued for 16 h. The solvent was evaporated and 2 M hydrochloric acid (200 ml) was added to the residue followed by slow addition of 10 M sodium hydroxide to adjust the pH to 5. The precipitated product was filtered off and washed subsequently with water and diethylether and dried to give 5-p-tolyl-pyrimidine-4,6-diol (17.7 g). $^1$H-NMR (300 MHz, d6-DMSO): 8.0(s, 1H); 7.4(d, 2H); 7.1(d, 2H); 2.25(s, 3H).

b) 5-p-tolyl-pyrimidine-4,6-diol (17.2 g) was dissolved in phosphorus oxychloride (250 ml) and N,N-dimethylaniline (25 ml) was added. The mixture was stirred at 70° C. for 16 h, then concentrated in vacuo. The residue was poured onto ice-water and extracted with diethylether (3×). The combined organic extracts were washed with 1N hydrochloric acid and with saturated sodium chloride solution, dried over magnesium sulfate, filtered and the filtrate was evaporated. The crude brown material was recrystallized from i-propanol to give 4,6-dichloro-5-p-tolyl-pyrimidine (13.5 g). $^1$H-NMR (CDCl$_3$): 8.78(s, 1H); 7.35(d, 2H); 7.20(d, 2H); 2.41(s, 3H).

c) 2-Phenylethanesulfonyl chloride was prepared by oxidising phenylethylmercaptan with N-chlorosuccinimide following the procedure given in [9].

d) A solution of 2-phenylethanesulfonyl chloride (40.94 g) in THF (250 ml) was cooled to −20° C. before it was treated with sat. aq. ammonia (50 ml). The brown suspension was stirred at rt for 16 h. The mixture was neutralised with aq. HCl and the organic solvent was evaporated. The remaining suspension was diluted with water and extracted four times with EA. The organic layers were combined and evaporated to give 2-phenyl-ethanesulfonic acid amide (33.06 g) as orange solid. $^1$H-NMR(300 MHz, CDCl$_3$): 3.15–3.21(m, 2H), 3.38–3.45(m, 2H), 4.59(s br, 2H), 7.21–7.37(m, 5H).

e) To a solution of 2-phenyl-ethanesulfonic acid amide (33.06 g) in methanol (300 ml) was added K.-tert.butylate (20.03 9). The resulting solution was stirred for 15 min before it was evaporated. The residue was washed with diethyl ether (400 ml) and dried under high vacuum to give 2-phenyl-ethanesulfonic acid amide potassium salt (37.93 g) as an orange powder.

f) A solution of 2-phenyl-ethanesulfonic acid amide potassium salt (3.0 g), 4,6-dichloro-5-p-tolyl-pyrimidine (2.15 g) and Hunig's base (1.57 ml) in DMSO (50 ml) was stirred at rt for 20 h before it was diluted with water (500 ml) and extracted twice with diethyl ether (250 ml). The aqueous phase was acidified with acetic acid. The resulting suspension was cooled to 5° C. and filtered. The solid material was washed with water and diethyl ether, and dried at 40° C. under high vacuum to give 2-phenyl-ethanesulfonic acid (6-chloro-5-p-tolyl-pyrimidin-4-yl)-amide (2.08 g) as a grey powder. LC-MS: $t_R$=5.23 min, $[M+1]^+$=388.18, $[M-1]^-$=386.14.

g) 2-Phenyl-ethanesulfonic acid (6-chloro-5-p-tolyl-pyrimidin-4-yl)-amide (850 mg) was added to a solution of K-tert. butylate (1.1 g) in ethylene glycol (15 ml). The mixture was stirred at 120° C. for 27 h before it was diluted with water (100 ml), acidified with 10% aq. citric acid (13 ml). The resulting precipitate was collected, washed with water and diethyl ether and dried to give 2-phenyl-ethanesulfonic acid [6-(2-hydroxy-ethoxy)-5-p-tolyl-pyrimidin-4-yl]-amide (716 mg) as a beige powder. LC-MS: $t_R$=4.44 min, $[M+1]^+$=414.18, $[M-1]^-$=412.13.

Referential Example 2

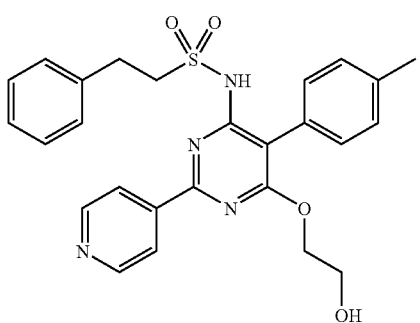

a) To a solution of sodium (0.23 g) in methanol (40 ml) was added 4-cyanopyridine (10.62 g) at room temperature. Stirring was continued for 6 h followed by the addition of ammoniumchloride (5.9 g) and stirring was continued for another 10 h. Then diethylether (120 ml) was added and the precipitate was filtered off after 30 min and washed once with diethylether (20 ml). The product was dried under high vacuum. 4-Amidino-pyridine hydrochloride (14.95 g) was obtained as a white powder.

b) A solution of sodium methylate (6.8 g) in methanol (200 ml) was cooled to 0° C. A solution of diethyl 2-(p-tolyl)-malonate (10.3 g) in methanol (50 ml) was slowly added. Upon completion of the addition the solution was allowed to come to room temperature and 4-amidino-pyridine hydrochloride (7.57 g) was added. The mixture was stirred at room temperature for 16 h. Eventually, the solvent was removed under reduced pressure and the remaining residue was dissolved in 2 M hydrochloric acid. The solution was extracted with diethyl ether, then adjusted to pH 5 with 10 M sodium hydroxide solution. A precipitate formed. The precipitate was collected, washed with cold water and dried at 60° C. under high vacuum. This gave 4,6-dihydroxy-2-(4-pyridyl)-5-(p-tolyl)-pyrimidine (8.77 g) (or a tautomer) as orange crystals.

c) To a mixture of 5-(p-tolyl)-4,6-dihydroxy-pyrimidine (8.0 g) and $POCl_3$ (100 ml), diethylamine (25 ml) was added at room temperature. The mixture was stirred for 16 h at 60° C. The excess of $POCl_3$ was distilled off under reduced pressure. The remaining oil was dissolved in DCM (300 ml) and treated with water (300 ml). The aqueous layer was separated and extracted three times with DCM. The combined organic layers were washed with water and brine, dried over $MgSO_4$ and evaporated. The resulting residue was suspended in isopropanol. The solid material was collected, washed with isopropanol, and diethyl ether and dried to give 4,6-dichloro-2-(4-pyridyl)-5-(p-tolyl)-pyrimidine (7.2 g) as a white crystalline powder. LC-MS: $t_R$=5.49 min, $[M+1]^+$=315.89.

d) A solution of 4,6-dichloro-2-(4-pyridyl)-5-(p-tolyl)-pyrimidine (1.5 g), 2-phenyl-ethanesulfonic acid amide potassium salt (1.44 g, Referential Example 1e) and Hunig's base (1 ml) in DMSO (20 ml) was stirred at rt for 24 h before it was diluted with water (150 ml) and extracted twice with diethyl ether. The aqueous layer was acidified with acetic acid. The precipitate was collected, and further purified by column chromatography on silica gel eluting with hexane:EA 1:1 to give 2-phenyl-ethanesulfonic acid (6-chloro-2-pyridin-4-yl-5-p-tolyl-pyrimidin-4-yl)-amide (480 mg) as a foam. LC-MS: $t_R$=5.08 min, $[M+1]^+$=465.13, $[M-1]^-$=462.96.

e) 2-Phenyl-ethanesulfonic acid (6-chloro-2-pyridin-4-yl-5-p-tolyl-pyrimidin-4-yl)-amide (480 mg) was added to a solution of K-tert. butylate (580 mg) in ethylene glycol (5 ml). The mixture was stirred at 11° C. for 72 h before it was diluted with water (100 ml), acidified with 10% aq. citric acid (13 ml). The resulting precipitate was collected, washed with water and diethyl ether and dried to give 2-phenyl-ethanesulfonic acid [6-(2-hydroxy-ethoxy)-2-pyridin-4-yl-5-p-tolyl-pyrimidin-4-yl]-amide as a beige powder. LC-MS: $t_R$=4.17 min, $[M+1]^+$=491.24, $[M-1]^-$=489.08.

Referential Example 3

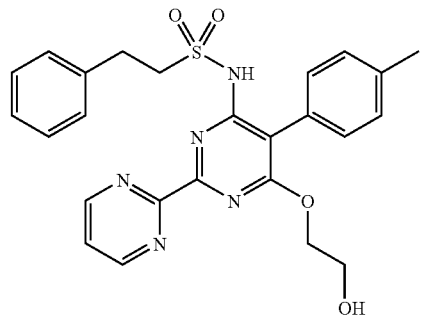

2-Phenyl-ethanesulfonic acid [6-(2-hydroxy-ethoxy)-5-p-tolyl-[2,2]bipyrimidinyl-4-yl]-amide was prepared following the procedures given in Referential Example 2 starting from 2-amidino-pyrimidine hydrochloride (e.g. EP 0 526 708 A1)-. LC-MS: $t_R$=4.42 min, $[M+1]^+$=492.30, $[M-1]^-$=490.27.

Referential Example 4

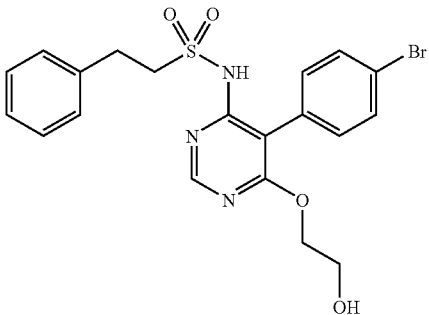

2-Phenyl-ethanesulfonic acid [5-(4-bromo-phenyl)-6-(2-hydroxy-ethoxy)-pyrimidin-4-yl]-amide was prepared in analogy to Referential Example 15 using 4-bromophenylacetic acid methyl ester instead of 4-chlorophenylacetic acid methyl ester in step a) and 2-phenyl-ethanesulfonic acid amide potassium salt instead of 2-thiophen-2-yl-ethanesulfonic acid amide potassium salt in step d). LC-MS: $t_R$=4.60 min, [M+1]$^+$=480.07, [M−1]$^-$=475.76.

Referential Example 5

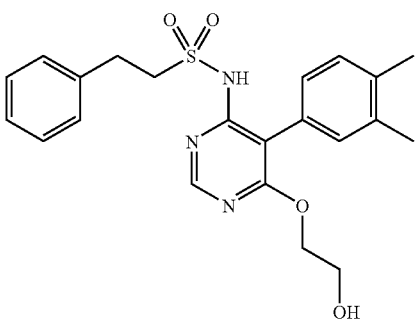

a) (In analogy to a procedure given in *J. Am. Chem. Soc.* 122 (2000), 1360-1370.) To a suspension of Pd(OAc)$_2$ (455 mg), 2-(di-tert.-butylphosphino)-biphenyl (1.21 g) and K$_3$PO$_4$ (39.6 g) in THF (200 ml) dimethylmalonate (12.85 g) and 1-bromo-3,4-dimethyl-benzene 15.0 g) was added under argon. The mixture was refluxed for 16 h, cooled to rt and diluted with EA (300 ml) and filtered. The filtrate was evaporated and the resulting brown oil was purified on silica gel eluting with heptane:EA 4:1 to 1:1 to give 2-(3,4-dimethyl-phenyl)-malonic acid dimethyl ester (16.2 g) as a colourless oil which slowly crystallises. $^1$H-NMR (300 MHz, CDCl$_3$): 2.25(s, 3H), 2.26(s, 3H), 3.75(s, 6H), 4.59(s, 1H), 7.10–7.20(m, 3H).

b) 2-Phenyl-ethanesulfonic acid [5-(3,4-dimethyl-phenyl)-6-(2-hydroxy-ethoxy)-pyrimidin-4-yl]-amide was prepared using the above 2-(3,4-dimethyl-phenyl)malonic acid dimethyl ester in analogy to Referential Example 1. LC-MS: $t_R$=4.61 min, [M+1]$^+$=428.19, [M−1]$^-$=426.07.

Referential Example 6

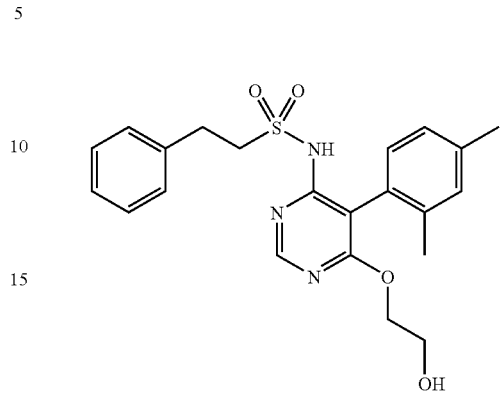

a) (In analogy to a procedure given in *J. Am. Chem. Soc.* 122 (2000), 1360–1370.) To a suspension of Pd(OAc)$_2$ (758 mg), 2-(di-tert.-butlylphosphino)-biphenyl (2.02 g) and K$_3$PO$_4$ (65.95 g) in THF (350 ml) dimethylmalonate (21.42 g) and 1-bromo-2,4-dimethyl-benzene (25 g) was added under argon. The mixture was refluxed for 96 h, cooled to rt and diluted with EA (300 ml) and filtered. The filtrate was evaporated and the resulting brown oil was purified on silica gel eluting with heptane:EA 4:1 to 1:1 followed by distillation (bp 95–100° C. at 0.064 mbar) to give 2-(2,4-dimethyl-phenyl)-malonic acid dimethyl ester (5.66 g) as a colourless oil. $^1$H-NMR(300 MHz, CDCl$_3$): 2.30(s, 6H), 3.75(s, 6H), 4.87(s, 1H), 6.98–7.05(m, 2H), 7.25–7.28(m, 1H).

b) 2-Phenyl-ethanesulfonic acid [5-(2,4-dimethyl-phenyl)-6-(2-hydroxy-ethoxy)pyrimidin-4-yl]-amide was prepared using the above 2-(2,4-dimethyl-phenyl)malonic acid dimethyl ester in analogy to the procedures given in Referential Example 1. LC-MS: $t_R$=4.54 min, [M+1]$^+$=428.23, [M−1]$^-$=426.07.

Referential Example 7

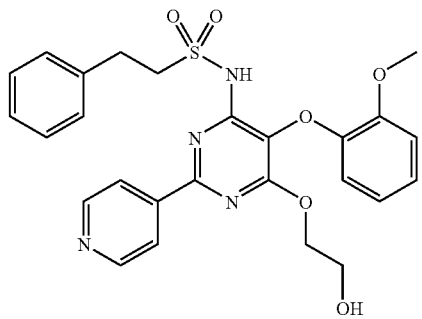

a) 2-methoxy-phenol (guaiacol) (48 ml) was slowly added to a stirred suspension of potassium carbonate (70.8 g) in acetone (480 ml) followed by heating to 45° C. Then dimethylchloromalonate (63.2 ml) in acetone (50 ml) was added within 20 min. The reaction mixture was heated to reflux for 16 h. The solvent was evaporated under reduced pressure, the residue taken into water and extracted with DCM. The combined organic layers were dried over sodium sulfate and evaporated. The oily product was crystallized from methyl-tert.-butyl-ether to give dimethyl-(2-methoxyphenoxy)malonate (86 g).

b) To a stirred solution of sodium methylate (9.7 g) in methanol (100 ml) a solution of dimethyl-(2-methoxyphenoxy)malonate (21.7 g) in methanol (50 ml) was added within 15 min and stirring was continued for 30 min followed by the addition of 4-amidino-pyridine hydrochloride (15 g, Referential Example 2) followed by stirring at room temperature for 20 h. The reaction mixture was concentrated in vacuo. The solid residue was stirred with diethyl ether. The obtained powder was filtered off and dissolved in water (300 ml). Acetic acid was added to pH=4. The precipitated product was filtered off, washed with water and dried in vacuo at 500C. 5-(o-methoxyphenoxy)4,6-dihydroxy-2-(4-pyridyl)pyrimidine (20.1 g, possibly also present as the tautomeric 5-(2-methoxyphenoxy)-2-(4-pyridyl)-tetrahydropyrimidine-4,6-dion) was obtained as a white powder.

c) 5-(2-methoxyphenoxy)4,6-dihydroxy-2-(4-pyridyl)-pyrimidine (10 g), N-ethyldiisopropylamine (11.2 g), tetraethylammoniumchloride (11 g) and phosphorus pentachloride (13.8 g) were dissolved in phosphorus oxychloride (25 ml) and heated to reflux for 3 h. The mixture was evaporated in vacuo, toluene was added and the mixture was again evaporated. The residue was taken into DCM and poured onto ice/water. The layers were separated, the organic layer was washed with water, dried over sodium sulfate and evaporated. After recrystallization from acetone, pure 4,6-dichloro-5-(2-methoxyphenoxy)-2-(4-pyridyl)-pyrimidine (6.52 g) was obtained.

d) A solution of 4,6-dichloro-5-(2-methoxyphenoxy)-2-(4-pyridyl)-pyrimidine (2 g) and 2-phenyl-ethanesulfonic acid amide potassium salt (2.82 g, Referential Example 1e) in DMF (50 ml) was stirred at rt for 16 h. Bulk of the solvent was evaporated before it was diluted with diethyl ether (50 ml). The mixture was acidified with 10% aq. citric acid. The precipitate that formed was collected, washed with diethyl ether (100 ml) and dried to give 2-phenyl-ethanesulfonic acid [6-chloro-5-(2-methoxy-phenoxy)-2-pyridin-4-yl-pyrimidin-4-yl]-amide (2.23 g) as a beige powder. LC-MS: $t_R$=4.93 min, $[M+1]^+$=497.22, $[M-1]^-$=494.96.

e) To a suspension of NaH (644 mg, 60% in mineral oil) in DME (15 ml) was added ethylene glycol (15 ml). After evolution of gas had ceased, 2-phenyl-ethanesulfonic acid [6-chloro-5-(2-methoxy-phenoxy)-2-pyridin-4-yl-pyrimidin-4-yl]-amide (800 mg) was added and the resulting solution was stirred at 90° C. for 16 h. A further portion of NaH (322 mg) was added and stirring was continued at 90° C. for 4 d. The mixture was diluted with EA (200 ml) and washed once with 10% aq. citric acid and 3 times with water. The organic phase was evaporated and the residue was suspended in diethyl ether. The solid material was collected, washed with diethyl ether and dried to give 2-phenyl-ethanesulfonic acid [6-(2-hydroxy-ethoxy)-5-(2-methoxyphenoxy)-2-pyridin-4-yl-pyrimidin-4-yl]-amide (513 mg) as a beige solid. LC-MS: $t_R$=4.05 min, $[M+1]^+$=523.10, $[M-1]^-$=521.24.

Referential Example 8

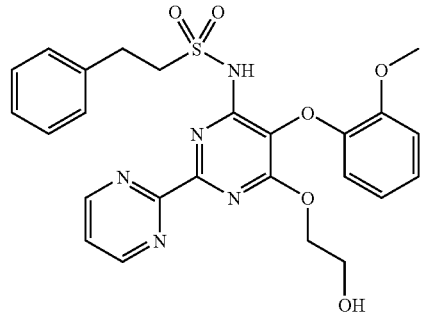

a) 2-Phenylethanesulfonic acid [6-chloro-5-(2-methoxyphenoxy)-2-(2-pyrimidinyl)-4-pyrimidinyl]-amide was prepared in analogy to Referential Example 7 from 4,6-dichloro-5-(2-methoxyphenoxy)-2-(2-pyrimidinyl)-pyrimidine (prepared as disclosed in [6]) and 2-phenylethane sulfonamide potassium salt (Referential Example 1). LC-MS: $t_R$=4.85 min, $[M+1]^+$=498.38, $[M-1]^-$= 496.19.

b) To a suspension of NaH (803 mg 60% dispersion in mineral oil) in DMF (15 ml) was carefully added ethylene glycol (15 ml). After the evolution of $H_2$-gas had stopped 2-phenylethanesulfonic acid [6-chloro-5-(2-methoxy-phenoxy)-2-(2-pyrimidinyl)-4-pyrimidinyl]-amide (1 g) was added. The resulting solution was heated to 90° C. and stirred for 16 h. The pale yellow solution was then cooled to rt, diluted with 10% aqueous citric acid solution (100 ml) and extracted three times with EA (50 ml). The combined organic layers were washed once more with 10% aqueous citric acid solution (50 ml) and brine (50 ml) and evaporated. The remaining residue was suspended in water (15 ml). The solid material was filtered off, washed with methanol (50 ml) followed by diethyl ether (50 ml) and dried. This gave 2-phenylethanesulfonic acid [6-(2-hydroxy-ethoxy)-5-(2-methoxy-phenoxy)-2-(2-pyrimidinyl)-4-pyrimidinyl]-amide (766 mg) as a white solid. LC-MS: $t_R$=4.32 min, $[M+1]^+$= 524.47, $[M-1]^-$=522.29.

Referential Example 9

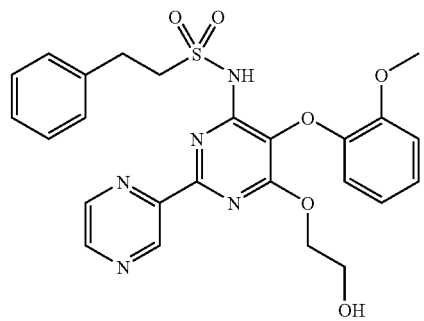

2-Phenyl-ethanesulfonic acid [6-(2-hydroxy-ethoxy)-5-(2-methoxy-phenoxy)-2-pyrazin-2-yl-pyrimidin-4-yl]-amide was prepared following the procedures given in

Referential Example 7 starting from 2-amidino-pyrazine hydrochloride. LC-MS: $t_R$=4.37 min, $[M+1]^+$=524.18, $[M-1]^-$=522.44.

Referential Example 10

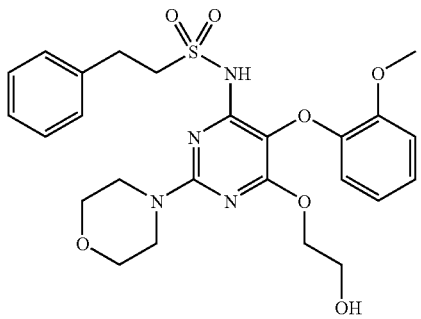

2-Phenyl-ethanesulfonic acid [6-(2-hydroxy-ethoxy)-5-(2-methoxy-phenoxy)-2-morpholin-4-yl-pyrimidin-4-yl]-amide was prepared following the procedures given in Referential Example 7 starting from morpholine-4-carboxamidine hydrobromide. LC-MS: $t_R$=4.75 min, $[M+1]^+$=531.25, $[M-1]^-$=529.50.

Referential Example 11

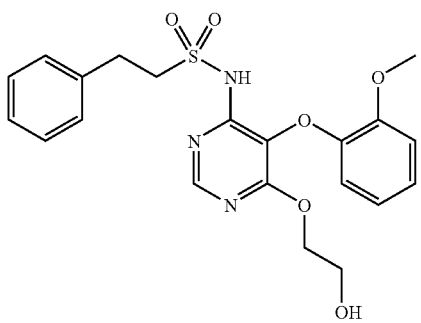

2-Phenyl-ethanesulfonic acid [6-(2-hydroxy-ethoxy)-5-(2-methoxy-phenoxy)-pyrimidin-4-yl]-amide was prepared following the procedures given in Referential Example 7 starting from formamidine hydrochloride. LC-MS: $t_R$=4.35 min, $[M+1]^+$=446.15, $[M-1]^-$=444.11.

Referential Example 12

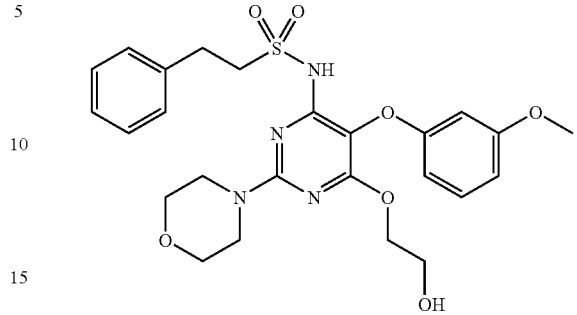

a) To a solution of 3-methoxyphenol (115 g) in acetone (1000 ml) was added $K_2CO_3$ (115 g). The suspension was stirred at 40° C. for 15 min. A solution of dimethylchloromalonate (133 ml) in acetone was added over a period of 45 min. The resulting brown suspension was stirred overnight at 70° C. Finally, the solvent was removed under reduced pressure and the residue was taken up in water (1000 ml) and extracted twice with DCM (500 ml). The combined organic layers were washed with water (500 ml), dried over $Na_2SO_4$, and evaporated to give crude dimethyl-(3-methoxyphenoxy)malonate (230 g) as an orange oil. The product was not purified any further.

b) To a solution of dimethyl-(3-methoxyphenoxy)-malonate (11.19 g) in methanol (100 ml) was added sodium methylate (6.48 g). The yellow solution was stirred for 6 h at rt. Then, morpholine-4-carboxamidine hydrobromide (8.40 g) was added and the mixture was stirred at rt for 16 h. The solvent was removed in vacuo and the residue was dissolved in water (150 ml) and extracted twice with diethyl ether (150 ml). The aqueous phase was acidified with 10% aq. citric acid. The solid that separated was collected, washed with water, evaporated twice from EA, and dried under high vacuum to give 5-(3-methoxy-phenoxy)-2-morpholin-4-yl-pyrimidine-4,6-diol (9.66 g) as a beige powder. LC-MS: $t_R$=2.88 min, $[M+1]^+$=320.19, $[M-1]^-$=318.02.

c) 5-(3-Methoxy-phenoxy)-2-morpholin-4-yl-pyrimidine-4,6-diol (9.66 g) was added portionwise to a mixture of $POCl_3$ (100 ml) and Hunig's base (50 ml). The black suspension was heated to 110C and stirred for 16 h. The mixture was cooled and N,N-dimethylaniline was added before heating was continued for another 24 h. Bulk of the solvents was evaporated and the remaining oil was poured into water. The dark solution was treated with charcoal before it was extracted twice with EA (300 ml). The organic phase was washed with brine and water, dried over $MgSO_4$ and evaporated. The remaining oil was chromatographed on silica gel eluting with heptane:EA. The product was recrystallised from 2-propanol, the pale yellow crystals were washed with diethyl ether to give 4-[4,6-dichloro-5-(3-methoxy-phenoxy)-pyrimidin-2-yl]-morpholine (7.48 g). LC-MS: $t_R$=5.56 min, $[M+1]^+$=355.99.

d) A solution of 4-[4,6-dichloro-5-(3-methoxy-phenoxy)-pyrimidin-2-yl]-morpholine (1.0 g) and 2-phenyl-ethanesulfonic acid amide potassium salt (1.57 g, Referential Example 1e) in DMSO (15 ml) was stirred at 60° C. for 24 h. The solution was diluted with water (75 ml) and extracted twice with diethyl ether (75 ml) before it was acidified with 10% aq. citric acid. The mixture was extracted twice with EA (150 ml). The organic phase was washed with water (50 ml). The product precipitated upon evaporation of the solvent. The solid was collected, washed with diethyl ether and dried to give 2-phenyl-ethanesulfonic acid [6-chloro-5-(3-methoxy-phenoxy)-2-morpholin-4-yl-pyrimidin-4-yl]-amide (1.28 g) as off-white powder. LC-MS: $t_R$=5.34 min, $[M+1]^+$=505.12, $[M-1]^-$=502.97.

e) A suspension of 2-phenyl-ethanesulfonic acid [6-chloro-5-(3-methoxy-phenoxy)-2-morpholin-4-yl-pyrimidin-4-yl]-amide (1.27 g) in ethylene glycol (12 ml) was treated with K-tert.-butylate (2.82 g). The resulting solution was stirred at 100° C. for 12 d. The solution was cooled to rt, diluted with 10% aq. citric acid (150 ml) and extracted twice with EA (150 ml). The organic phase was washed with water (50 ml) and evaporated. The crude product was purified by chromatography on silica gel eluting with heptane:EA 1:1 to 1:2 to furnish 2phenyl-ethanesulfonic acid [6-(2-hydroxy-ethoxy)-5-(3-methoxy-phenoxy)-2-morpholin-4-yl-pyrimidin-4-yl]-amide (1.1 g) as a white solid. LC-MS: $t_R$=4.66 min, $[M+1]^+$=531.20, $[M-1]^-$=529.14.

Referential Example 13

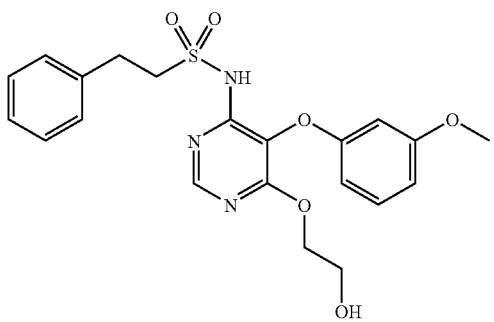

2-Phenyl-ethanesulfonic acid [6-(2-hydroxy-ethoxy)-5-(3-methoxy-phenoxy)-pyrimidin-4-yl]-amide was prepared following the procedures given in Referential Example 12 starting from formamidine hydrochloride. $^1$H-NMR (300 MHz, CDCl$_3$): 3.14–3.21(m, 2H), 3.70–3.74(m, 2H), 3.79(s, 3H), 3.94–4.01(m, 2H), 4.40–4.46 (m, 2H), 6.41(dd, J=2.4, 8.4, 1H), 6.47(t, J=2.4, 1H), 6.66(dd, J=1.8, 8.4, 1H), 7.16–7.32(m, 6H), 8.37(s, 1H); LC-MS: $t_R$=4.33 min, $[M+1]^+$=446.27, $[M-1]^-$=444.05.

Referential Example 14

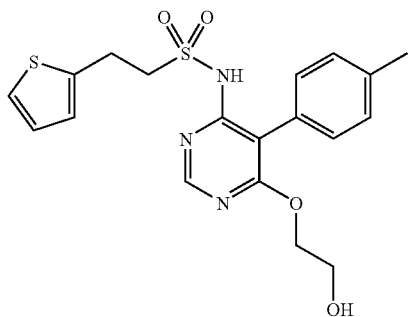

a) 2-Thiophen-2-yl-ethanesulfonyl chloride was obtained starting from commercial 2-(2-bromo-ethyl)-thiophene following the procedures given in the literature (J. Am. Chem. Soc. 103 (1981),1525–1533).

b) A solution of crude 2-thiophen-2-yl-ethanesulfonyl chloride (25 g) in THF (400 ml) was treated with sat. aq. ammonia (60 ml) at 0° C. The mixture was stirred at rt for 16 h before it was neutralised with 25% aq. HCl (60 ml). Bulk of the THF was evaporated. The aq. solution was extracted twice with EA. The organic phase was washed with water and evaporated. The remaining oil was purified by chromatography on silica gel eluting with heptane:EA 1:1. The product was further purified by recrystallisation from diethyl ether/pentane to give 2-thiophen-2-yl-ethanesulfonic acid amide (8.46 g) as off-white crystals. $^1$H-NMR (300 MHz, CDCl$_3$): 3.36–3.50(m, 4H), 4.54(s br, 2H), 6.89–6.92(m, 1H), 6.95(dd, J=3.5, 5.1, 1H), 7.20(dd, J=1.1, 5.0, 1H).

c) A solution of 2-thiophen-2-yl-ethanesulfonic acid amide (3.77 g) in methanol (200 ml) was treated with K-tert.-butylate (2.21 g), stirred at rt for 15 min, evaporated and dried under high vacuum to give 2-thiophen-2-yl-ethanesulfonic acid amide potassium salt (4.5 g) as a beige powder.

d) 2-Thiophen-2-yl-ethanesulfonic acid [6-(2-hydroxy-ethoxy)-5-p-tolyl-pyrimidin-4-yl]-amide was prepared using the above 2-thiophen-2-yl-ethanesulfonic acid amide potassium salt following the procedures given in Referential Example 1. $^1$H-NMR(300 MHz, CDCl$_3$): 2.42(s, 3H), 3.33–3.41(m, 2H), 3.81–3.86(m, 2H), 3.994.07(m, 2H), 4.46–4.51(m, 2H), 6.82–6.86(m, 1H), 6.92(dd, J=3.5, 5.1, 1H), 7.13–7.18(m, 3H), 7.28–7.32(m 2H), 8.51(s, 1H); LC-MS: $t_R$=4.18 min, $[M+1]^+$=420.24, $[M-1]^-$=418.20.

Referential Example 15

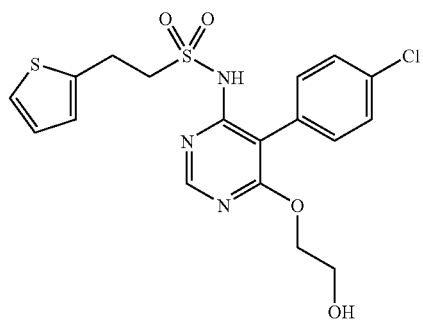

a) At 35° C. a solution of 4-chlorophenylacetic acid methyl ester (52 g) in THF (170 ml) was carefully added over a period of 70 min to a suspension of NaH (15.6 g) in dry THF (550 ml). Stirring was continued for 40 min without heating and the temperature dropped to 290C. The evolution of gas had stopped before dimethylcarbonate (94.8 ml) was added dropwise while the temperature of the mixture was maintained at 25–28° C. After the evolution of gas had ceased, the mixture was diluted with THF (200 ml) and stirring was continued for 72 h at rt. The mixture was carefully acidified with aq. HCl before bulk of the THF was removed in vacuo. The residue was dissolved in diethyl ether (1200 ml), washed three times with 1 N aq. HCl and once with brine, dried over MgSO$_4$ and evaporated. The residue formed was collected, washed with diethyl ether and dried to give 2-(4-chloro-phenyl)-malonic acid dimethyl ester (42 g) as white crystals.

b) A solution of 2-(4-chlorophenyl)-malonic acid dimethyl ester (18.90 g) in methanol (200 ml) was added dropwise at 0° C. to a solution sodium methylate (14.60 g) in methanol (150 ml). The mixture was stirred for 1 h at 0° C. before formamidine hydrochloride (7.66 g) was added. The suspension was stirred at rt for 20 h. The solvent was removed and the residue was suspended in 2 N aq. HCl (200 ml). The pH of the suspension was carefully adjusted to 4–5 by adding 10 M NaOH (20 ml), stirring was continued for 30 min. The white precipitate was collected, washed with water and diethyl ether and dried to give 5-(4-chlorophenyl)-pyrimidine-4,6-diol (16.44 g) as a white powder. LC-MS: $t_R$=2.75 min, [M+H]+=222.96, [M–H]$^-$=220.92.

c) To a suspension of 5-(4-chlorophenyl)-pyrimidine-4,6-diol (16.44 g) in POCl$_3$ (165 ml) was carefully added N,N-dimethylaniline (16.5 ml). The mixture was refluxed for 1.5 h. The dark green solution was evaporated and the residue was poured onto ice/water. The suspension was diluted with 2 N HCl (200 ml) and water (800 ml) and stirred at 2°C. for 1 h. The precipitate was collected, washed with water and dried to give 4,6-dichloro-5-(4-chlorophenyl)-pyrimidine (18.66 g) as a slightly green powder.

d) A solution of 4,6-dichloro-5-(4-chlorophenyl)pyrimidine (848 mg), 2-thiophen-2-yl-ethanesulfonic acid amide potassium salt (1.5 g, Referential Example 14) and Hunig's base (1 ml) in DMSO (20 ml) was stirred at rt for 24 h before it was diluted with water (200 ml) and extracted twice with diethyl ether. The aqueous layer was acidified with acetic acid. The precipitate was collected, washed with water and diethyl ether and dried to give 2-thiophen-2-yl-ethanesulfonic acid [6-chloro-5-(4-chloro-phenyl)-pyrimidin-4-yl]-amide (930 mg) as a beige powder. LC-MS: $t_R$=5.01 min, [M+1]$^+$=413.49, [M–1]$^-$=411.93.

e) 2-Thiophen-2-yl-ethanesulfonic acid [6-chloro-5-(4-chloro-phenyl)-pyrimidin-4-yl]-amide (930 mg) was added to a solution of K-tert. butylate (1.16 g) in ethylene glycol (10 ml). The mixture was stirred at 110° C. for 12 h before it was diluted with water (150 ml), acidified with 10% aq. citric acid (13 ml). The resulting precipitate was collected, washed with water and diethyl ether and dried to give (820 mg) 2-thiophen-2-yl-ethanesulfonic acid [5-(4-chloro-phenyl)-6-(2-hydroxy-ethoxy) -pyrimidin-4-yl]-amide as a beige powder. LC-MS: $t_R$=4.43 min, [M+1]$^+$=440.01, [M–1]$^-$=437.99.

Referential Example 16

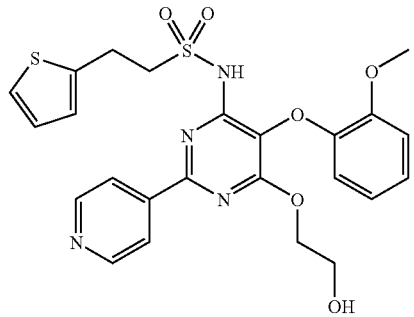

2-Thiophen-2-yl-ethanesulfonic acid [6-(2-hydroxy-ethoxy)-5-(2-methoxy-phenoxy)-2-pyridin-4-yl-pyrimidin-4-yl]-amide was prepared following the procedures given in Referential Example 7 using 2-thiophen-2-yl-ethanesulfonic acid amide potassium salt (Referential Example 14).; LC-MS: $t_R$=4.00 min, [M+1]$^+$=529.29, [M–1]$^-$=526.97.

Referential Example 17

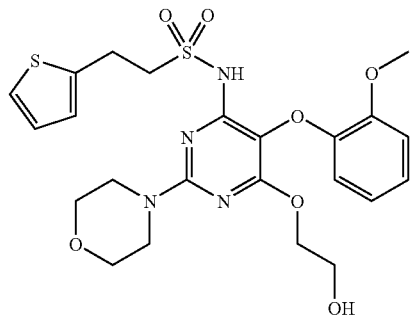

2-Thiophen-2-yl-ethanesulfonic acid [6-(2-hydroxy-ethoxy)-5-(2-methoxy-phenoxy)-2-morpholin-4-yl-pyrimidin-4-yl]-amide was prepared following the procedures given in Referential Example 10 using 2-thiophen-2-yl-ethanesulfonic acid amide potassium salt (Referential Example 14).; LC-MS: $t_R$=4.62 min, [M+1]$^+$=537.21, [M–1]$^-$=534.96.

Referential Example 18

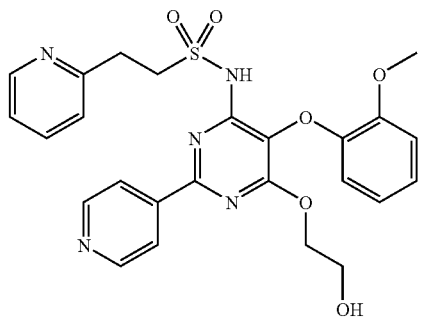

a) 2-Pyridin-2-yl-ethanesulfonyl chloride hydrochloride was prepared starting from commercial 2-pyridine-2-ethane sulfonic acid following the procedure given in *J. Med. Chem.* 36 (1993), 320–330.

b) 2-Pyridin-2-yl-ethanesulfonic acid amide potassium salt was prepared using the above 2-pyridin-2-yl-ethanesulfonyl chloride hydrochloride following the procedures given in Referential Example 14 b and 14c.

c) A solution of 4,6-dichloro-5-(2-methoxyphenoxy)-2-(4-pyridyl)-pyrimidine (1.75 g, Referential Example 7) and 2-pyridin-2-yl-ethanesulfonic acid amide potassium salt (1.13 g) in DMSO (30 ml) was stirred at rt for 24 h. Triethylamine (657 mg) was added and stirring was continued for another 96 h before the mixture was diluted with ethyl acetate (150 ml) and washed 4% aq. citric acid and water. The aqueous phase was extracted three more times with EA. The organic phase was dried over MgSO$_4$ and evaporated. The crude product was purified by column chromatography on silica gel eluting with EA containing 0–10% methanol to give 2-pyridin-2-yl-ethanesulfonic acid [6-chloro-5-(2-methoxyphenoxy)-2-pyridin-4-yl-pyrimidin-4-yl]-amide (950 mg) as a brown powder. LC-MS: $t_R$=3.63 min, [M+1]$^+$=498.31, [M−1]$^-$=496.10.

d) To a suspension of NaH (701 mg, 60% in mineral oil) in DMF (15 ml) was added ethylene glycol (15 ml). After the evolution of gas had ceased, 2-pyridin-2-yl-ethanesulfonic acid [6-chloro-5-(2-methoxy-phenoxy)-2-pyridin-4-yl-pyrimidin-4-yl]-amide (800 mg) was added and the resulting solution was stirred at 90° C. for 40 h. The solution was neutralised with 2 N aq. HCl (7 ml) before it was evaporated. The brown residue was purified by chromatography on prep. tlc-plates with EA:methanol:sat. aq. ammonia 10:2:1. The product was further purified by crystallisation from methanol:diethyl ether:pentane to give 2-pyridin-2-yl-ethanesulfonic acid [6-(2-hydroxy-ethoxy)-5-(2-methoxy-phenoxy)-2-pyridin-4-yl-pyrimidin-4-yl]-amide (280 mg) as beige crystals. $^1$H-NMR(300 MHz, CDC$_3$): 3.36–3.43(m, 2H), 3.86–3.90(m, 2H), 3.94(s, 3H), 4.23–4.30(m, 2H), 4.564.62(m, 2H), 6.91(dt, Jd=1.5, Jt=7.7, 1H, 7.00(dd, J=1.7, 8.2, 1H, 7.08–7.20(m, 4H), 7.57(dt, Jd=1.8, Jt=7.9, 1H), 8.15(dd, J=1.7, 4.6, 2H), 8.43(d, J=4.4, 1H), 8.72(dd, J=1.7, 4.6, 2H); LC-MS: $t_R$=3.23 min, [M+1]$^+$=524.48, [M−1]$^-$=522.25.

Referential Example 19

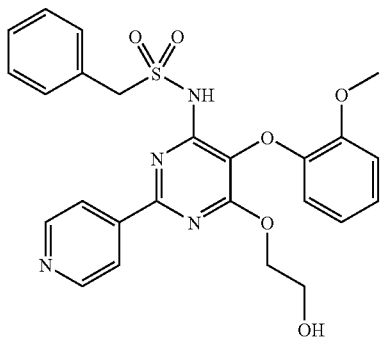

a) Phenyl-methanesulfonamide potassium salt was prepared in analogy to the procedures given in Referential Example 1d and 1e using commercial phenyl-methanesulfonyl chloride. $^1$H-NMR(300 MHz, DSMO): 3.73(s, 2H), 7.13–7.30(m, 5H).

b) N-[6-(2-Hydroxy-ethoxy)-5-(2-methoxy-phenoxy)-2-pyridin-4-yl-pyrimidin-4-yl]-C-phenyl-methanesulfonamide was prepared in analogy to Referential Example 7 using the above phenyl-methanesulfonamide potassium salt. LC-MS: $t_R$=3.99 min, [M+1]$^+$=509.32, [M−1]$^-$=507.31.

Referential Example 20

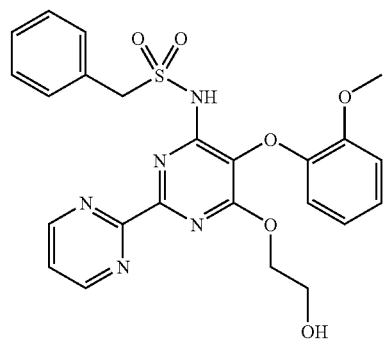

N-[6-(2-Hydroxy-ethoxy)-5-(2-methoxy-phenoxy)-[2,2']bipyrimidinyl-4-yl]-C-phenyl-methanesulfonamide was prepared in analogy to Referential Example 8 using phenyl-methanesulfonamide potassium salt (Referential Example 19). LC-MS: $t_R$=4.15 min, [M+1]$^+$=510.34, [M−1]$^-$=508.54.

Referential Example 21

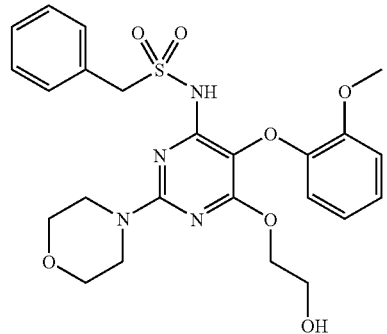

N-[6-(2-Hydroxy-ethoxy)-5-(2-methoxy-phenoxy)-2-morpholin-4-yl-pyrimidin-4-yl]-C-phenyl-methanesulfonamide was prepared in analogy to Referential Example 10 using phenyl-methanesulfonamide potassium salt (Referential Example 19). LC-MS: $t_R$=4.54 min, [M+1]$^+$=517.32, [M−1]$^-$=515.07.

Referential Example 22

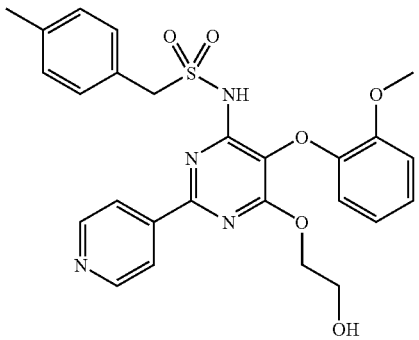

a) p-Tolyl-methanesulfonyl chloride was prepared by oxidising commercially available p-tolyl-methanethiol with N-chlorosuccinimide in analogy to the procedure disclosed in [9].

b) p-Tolyl-methanesulfonamide potassium salt was prepared in analogy to the procedures given in Referential Example 1d and 1e. $^1$H-NMR(300 MHz, CDCl$_3$) (sulfonamide): 2.36(s, 3H), 4.27(s, 2H), 4.63(s br, 2H), 7.20(d, J=7.9, 2H), 7.30(d, J=8.1, 2H).

c) N-[6-(2-Hydroxy-ethoxy)-5-(2-methoxy-phenoxy)-2-pyridin-4-yl-pyrimidin-4-yl]-C-p-tolyl-methanesulfonamide was prepared using the above p-tolyl-methanesulfonamide potassium salt in analogy to the procedures given in Referential Example 7. LC-MS: $t_R$=4.18 min, [M+1]$^+$= 523.22, [M−1]$^−$=521.19.

Referential Example 23

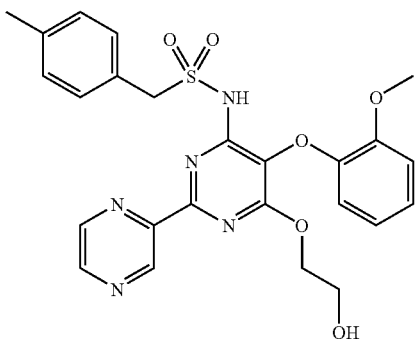

N-[6-(2-Hydroxy-ethoxy)-5-(2-methoxy-phenoxy)-2-pyrazin-2-yl-pyrimidin-4-yl]-C-p-tolyl -methanesulfonamide was prepared using the above p-tolyl-methanesulfonamide potassium salt in analogy to the procedures given in Referential Example 9. LC-MS: $t_R$=4.46 min, [M+1]$^+$= 524.20, [M−1]$^−$=521.93.

Referential Example 24

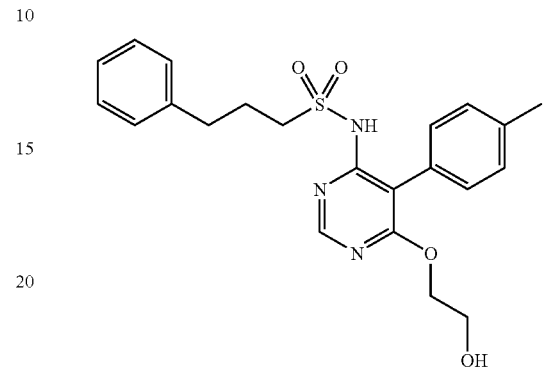

a) 3-Phenyl-propane-1-sulfonyl chloride was prepared by oxidising commercially available 3-phenyl-propane-1-thiol with N-chlorosuccinimide in analogy to the procedure disclosed in [9].

b) 3-Phenyl-propane-1-sulfonic acid amide potassium salt was prepared in analogy to the procedures given in Referential Example 1d and 1e. $^1$H-NMR (300 MHz, CDCl$_3$) (sulfonamide): 2.11–2.23(m, 2H), 2.76(t, J=7.5, 2H), 3.05–3.13(m, 2H), 4.85(s br, 2H), 7.14–7.40(m, 5H).

c) 3-Phenyl-propane-1-sulfonic acid [6-(2-hydroxy-ethoxy)-5-p-tolyl-pyrimidin-4-yl]-amide was prepared in analogy to the procedures given in Referential Example 1 using the above 3-phenyl-propane-1-sulfonic acid amide potassium salt. LC-MS: $t_R$=4.66 min, [M+1]$^+$=428.24, [M−1]$^−$=426.21.

Referential Example 25

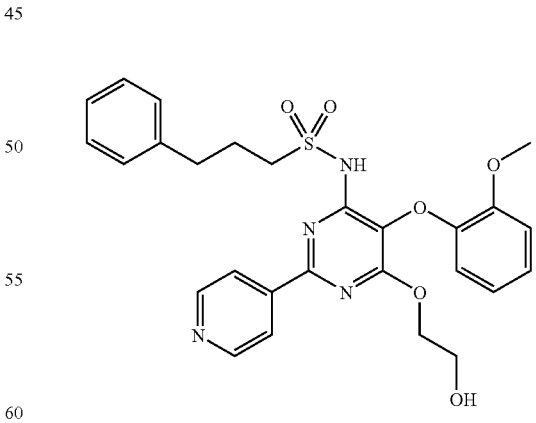

3-Phenyl-propane-1-sulfonic acid [6-(2-hydroxy-ethoxy)-5-(2-methoxy-phenoxy)-2-pyridin-4-yl-pyrimid-4yl]-amide was prepared in analogy to the procedures given in Referential Example 7 using 3-phenyl-propane-1-sulfonic acid amide potassium salt of Referential Example 24. LC-MS: $t_R$=4.14 min, [M+1]$^+$=537.45, [M−1]$^−$=535.41.

Referential Example 26

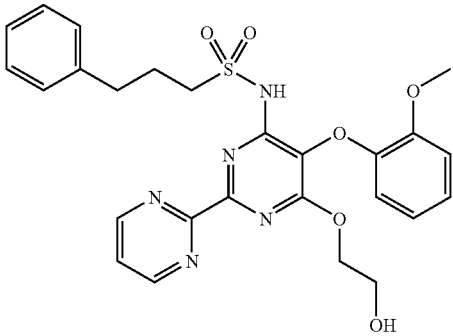

3-Phenyl-propane-1-sulfonic acid [6-(2-hydroxy-ethoxy)-5-(2-methoxy-phenoxy)-[2,2]bipyrimidinyl-4-yl]-amide was prepared in analogy to the procedures given in Referential Example 8 using 3-phenyl-propane-1-sulfonic acid amide potassium salt of Referential Example 24. LC-MS: $t_R$=4.37 min, [M+1]$^+$=538.38, [M−1]$^-$=536.27.

Referential Example 27

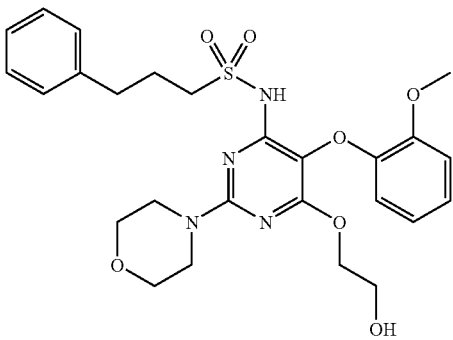

3-Phenyl-propane-1-sulfonic acid [6-(2-hydroxy-ethoxy)-5-(2-methoxy-phenoxy)-2-morpholin-4-yl-pyrimidin-4-yl]-amide was prepared in analogy to the procedures given in Referential Example 10 using 3-phenyl-propane-1-sulfonic acid amide potassium salt of Referential Example 24. LC-MS: $t_R$=4.80 min, [M+1]$^+$=545.40, [M−1]$^-$=543.52.

Referential Example 28

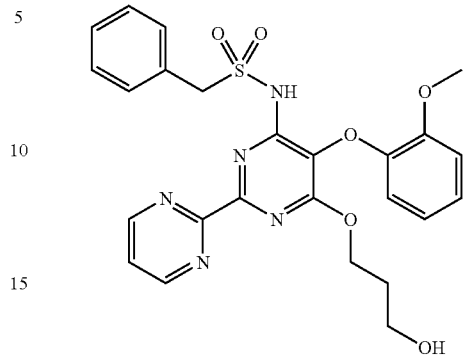

N-[6-(3-Hydroxy-propoxy-5-(2-methoxy-phenoxy)-[2,2']bipyrimidinyl-4-yl]-C-phenyl-methanesulfonamide was prepared in analogy to the procedures given in Referential Example 20 using propane-1,3-diol instead of ethylene glycol. LC-MS: $t_R$=4.13 min, [M+1]$^+$=524.34, [M−1]$^-$=522.19.

Referential Example 29

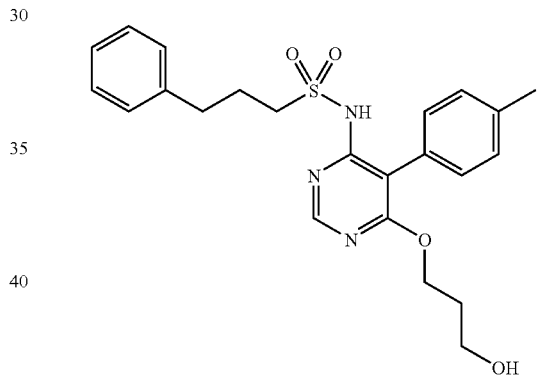

3-Phenyl-propane-1-sulfonic acid [6-(3-hydroxy-propoxy)-5-p-tolyl-pyrimidin-4-yl]-amide was prepared in analogy to the procedures given in Referential Example 24 using propane-1,3-diol instead of ethylene glycol. LC-MS: $t_R$=4.72 min, [M+1]$^+$=442.28, [M−1]$^-$=440.22.

EXAMPLES

The following examples illustrate the invention but do not at all limit the scope thereof.

The following reagents have been synthesised in order to prepare the examples listed below according to or in analogy to literature procedures: 5-bromo-2-chloro-pyrimidine (*Aust. J. Chem.* 17 (1964), 794–802; *J. Org. Chem.* 25 (1960), 1916–1919); 2,5-dichloro-pyrimidine (in analogy to 5-bromo-2-chloro-pyrimidine using chlorine instead of bromine); 2-chloro-5-methyl-pyrimidine (*J. Med. Chem.* 6 (1963), 697–701; *Aust. J. Chem.* 30 (1977), 2515–2525); 2-methanesulfonyl-5-methoxy-pyrimidine (*J. Chem. Soc. Perkin Trans.* 1, 1999, 3265–3268; *J. Org. Chem.* 27 (1962), 3614–3617); 2-chloro-5-methylsulfanyl-pyrimidine (*Il Farmaco* 43 (1988), 277–292; French Patent 1 549 494 (1968));

2-methanesulfonyl-5-trifluoromethyl-pyrimidine (*Tetrahedron Lett.* 37 (1996), 1829–1832); 2-methanesulfonyl-4,6-dimethoxy-pyrimidine was prepared starting from 4,6-dichloro-2-methylsulfanyl-pyrimidine using standard methodology.

All other reagents constitute commercially available ingredients.

Example 1

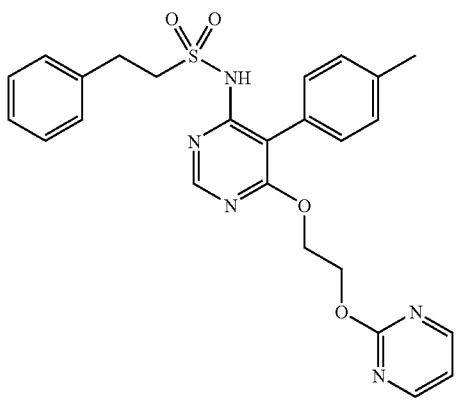

To sodium hydride (50 mg, 60% in mineral oil) was added THF (25 ml) followed by 2-phenyl-ethanesulfonic acid [6-(2-hydroxy-ethoxy)-5-p-tolyl-pyrimidin-4-yl]-amide (150 mg, Referential Example 1). The mixture was stirred for 1 h at rt before 2-chloro-pyrimidine (86 mg) was added. Stirring was continued for 17 h at 80° C. The solvent was evaporated and diethylether (20 ml) was added to the residue. The precipitate was filtered off and washed with diethylether, dissolved in water (20 ml) and acidified with citric acid and extracted twice with EA (50 ml). The organic phase was washed with water, dried over Na$_2$SO$_4$ and evaporated. The residue is suspended in 2-propanol (15 ml) and stirred at 70° C. for 10 min and cooled to 0° C. before the solid material is collected, washed with 2-propanol (2 ml) and dried under high vacuum to furnish 2-phenyl-ethanesulfonic acid {6-[2-(pyrimidin-2-yloxy)-ethoxy]-5-p-tolyl-pyrimidin-4-yl}-amide (133 mg) as a white powder. LC-MS: $t_R$=4.97 min, [M+1]$^+$=492.34, [M−1]$^-$=490.28.

Example 2

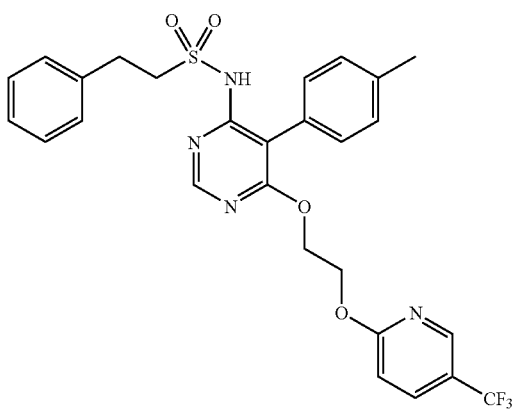

To sodium hydride (27 mg, 60% in mineral oil) was added THF (15 ml) followed by 2-phenyl-ethanesulfonic acid [6-(2-hydroxy-ethoxy)-5-p-tolyl-pyrimidin-4-yl]-amide (80 mg, Referential Example 1). The mixture was stirred for 1 h at rt before 2-chloro-5-trifluoromethyl-pyridine (86 mg) was added. Stirring was continued for 17 h at 80° C. The solvent was evaporated, the residue was dissolved in water (20 ml), acidified with citric acid. The suspension was treated with hexane (15 ml). The solid material was collected, washed with hexane:EA 1:1 (20 ml) and dried to yield 2-phenyl-ethanesulfonic acid {5-p-tolyl-6-[2-(5-trifluoromethyl-pyridin-2-yloxy)-ethoxy]-pyrimidin-4-yl}-amide (96 mg) as beige powder. LC-MS: $t_R$=5.86 min, [M+1]$^+$=559.20, [M−1]$^-$=557.37.

Example 3

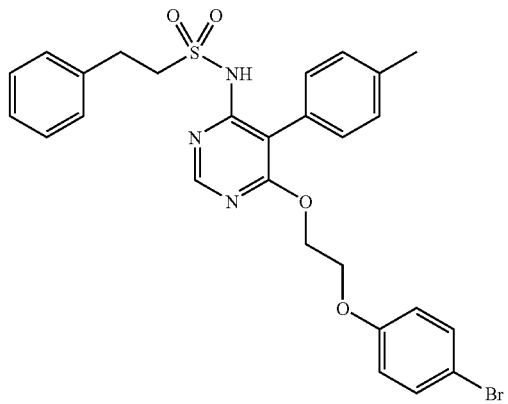

To a suspension of NaH (17 mg, 60% in mineral oil) in DME (5 ml) was added 2-(4-bromo-phenoxy)-ethanol (111 mg). The mixture was stirred at 50° C. for 1 h before 2-phenyl-ethanesulfonic acid (6-chloro-5-p-tolyl-pyrimidin-4-yl)-amide (100 mg, Referential Example 1f) and K-tert.-butylate (25 mg) was added. The mixture was stirred at 70° C. for 16 h. A further portion of K-tert.-butylate (50 mg) was added and stirring was continued at 70° C. for 12 h and at rt for 72 h. The solvent was evaporated. The residue was treated with water (40 ml), acidified with 10% aq. citric acid and extracted twice with EA (50 ml). The organic phase was washed with water and evaporated. The crude product was crystallised from 2-propanol to give 2-phenyl-ethanesulfonic acid {6-[2-(4-bromo-phenoxy)-ethoxy]-5-p-tolyl-pyrimidin-4-yl}-amide (127 mg) as a beige powder. LC-MS: $t_R$=6.14 min, [M+1]$^+$=568.38, [M−1]$^-$=570.15.

Example 4

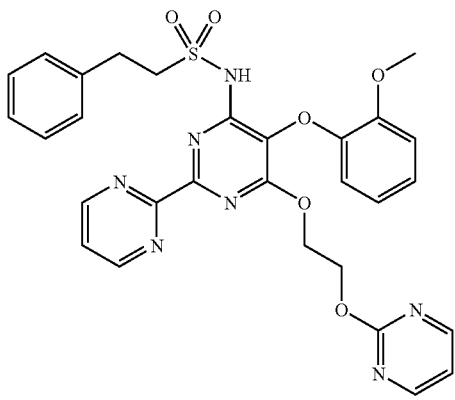

To a suspension of NaH (29 mg 60% dispersion in mineral oil) in a mixture of DMF and THF (2.5 ml each) was added 2-phenylethanesulfonic acid [6-(2-hydroxy-ethoxy)-5-(2-methoxy-phenoxy)-2-(2-pyrimidinyl)-4-pyrimidinyl]-amide (150 mg). After gas-evolution had ceased, 2-chloropyrimidine (82 mg) was added. The resulting pale yellow suspension was stirred at 70° C. for 4 h. It was cooled to rt, diluted with EA (75 ml) and washed with 10% aqueous citric acid solution (50 ml) followed by water (50 ml). The organic layer was evaporated and the remaining residue was purified on prep. tlc plates (silica gel, 0.5 mm layer thickness) developing with EA:methanol:sat. aqueous ammonia 8:2:1. This furnished 2-phenylethanesulfonic acid {5-(2-methoxy-phenoxy)-6-[2-(pyrimidin-2-yloxy)-ethoxy]-2-(2-pyrimidinyl)-4-pyrimidinyl}-amide as a pale yellow powder. LC-MS: $t_R$=4.60 min, $[M+1]^+$=602.69, $[M-1]^-$=600.43.

Example 5

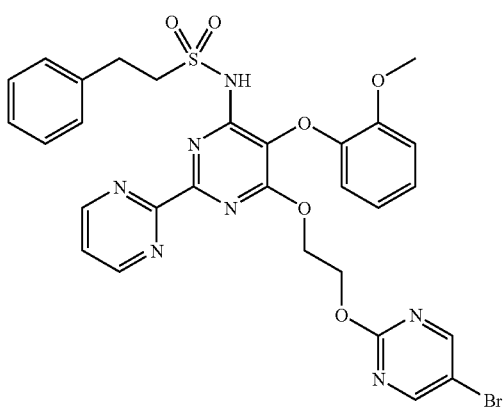

To a suspension of NaH (29 mg 60% dispersion in mineral oil) in a mixture of DMF and THF (2.5 ml each) was added 2-phenylethanesulfonic acid [6-(2-hydroxy-ethoxy)-5-(2-methoxy-phenoxy)-2-(2-pyrimidinyl)-4-pyrimidinyl]-amide (150 mg). After gas-evolution had ceased, 2-chloro-5-bromopyrimidine (138 mg) was added. The resulting orange suspension was stirred at 700C for 4 h. A further portion of NaH (29 mg 60% dispersion in mineral oil) followed by 2-chloro-5-bromopyrimidine (138 mg) was added. Heating and stirring was continued for 25 h. Eventually, the reaction mixture was cooled to rt, diluted with EA (75 ml) and washed with 10% aqueous citric acid solution (50 ml) followed by water (50 ml). The organic layer was evaporated and the remaining residue was purified on prep. tlc plates (silica gel, 0.5 mm layer thickness) developing with EA:methanol:sat. aqueous ammonia 8:2:1. This furnished 2phenylethanesulfonic acid {5-(2-methoxy-phenoxy)-6-[2-(5-bromopyrimidin-2-yloxy)-ethoxy]-2-(2-pyrimidinyl)-4-pyrimidinyl}-amide as a pale yellow powder. LC-MS: $t_R$=5.11 min, $[M+1]^+$=680.23, $[M-1]^-$=678.36.

Example 6

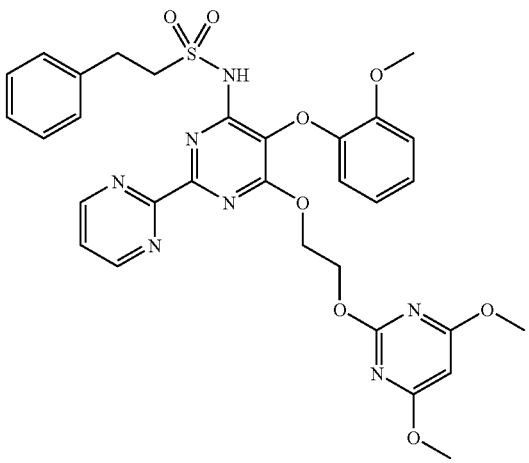

To a suspension of NaH (29 mg, 60% dispersion in mineral oil) in a mixture of DMF and THF (2.5 ml each) was added 2-phenylethanesulfonic acid [6-(2-hydroxy-ethoxy)-5-(2-methoxy-phenoxy)-2-(2-pyrimidinyl)-4-pyrimidinyl]-amide (150 mg). After gas-evolution had ceased, 4,6-dimethoxy-2-methylsulfonylpyrimidine (156 mg) was added. The resulting yellow suspension was stirred at 70° C. for 4 h. Eventually, the reaction mixture was cooled to rt, diluted with EA (75 ml) and washed with 10% aqueous citric acid solution (50 ml) followed by water (50 ml). The organic layer was evaporated and the remaining residue was purified on prep. tlc plates (silica gel, 0.5 mm layer thickness) developing with EA:methanol:sat. aqueous ammonia 8:2:1. This furnished 2-phenylethanesulfonic acid {5-(2-methoxy-phenoxy)-6-[2-(4,6-dimethoxy-pyrimidin-2-yloxy)-ethoxy]-2-(2-pyrimidinyl)-4-pyrimidinyl}-amide as a pale yellow powder. LC-MS: $t_R$=5.21 min, $[M+1]^+$=662.69, $[M-1]^-$=660.23.

Example 7–86

The Examples represented in Table 1 to Table 8 have been prepared in analogy to the Examples 1 to 6 using the Referential Examples 1 to 29 as starting materials.

TABLE 1
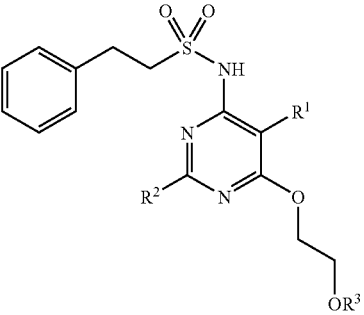
| Ex. No | Ref. Ex. No | R¹ | R² | R³ | LC-MS |
|---|---|---|---|---|---|
| 7 | 1 | 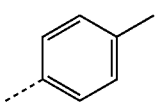 | H | 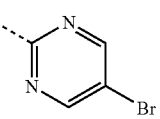 | $t_R$ = 5.41 min<br>$[M + H]^+$: 570.22<br>$[M - H]^-$: 568.16 |
| 8 | 1 | 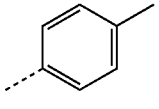 | H | 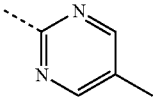 | $t_R$ = 5.11 min<br>$[M + H]^+$: —<br>$[M - H]^-$: 504.11 |
| 9 | 2 | 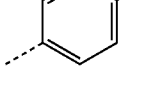 | 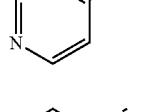 | 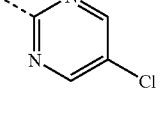 | $t_R$ = 5.26 min<br>$[M + H]^+$: 530.32<br>$[M - H]^-$: — |
| 10 | 2 | 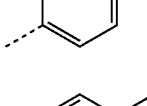 | 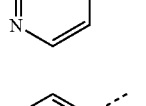 | 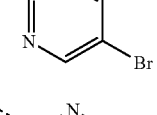 | $t_R$ = 5.21 min<br>$[M + H]^+$: 647.10<br>$[M - H]^-$: 646.54 |
| 11 | 2 | 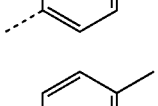 | 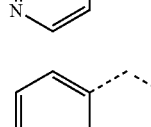 | 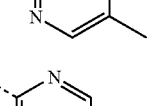 | $t_R$ = 4.84 min<br>$[M + H]^+$: 583.22<br>$[M - H]^-$: 581.18 |
| 12 | 2 | 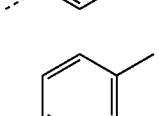 | 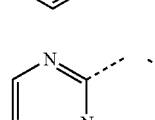 | 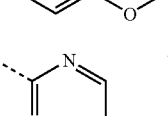 | $t_R$ = 4.82 min<br>$[M + H]^+$: 599.34<br>$[M - H]^-$: 597.45 |
| 13 | 3 | 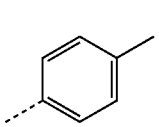 | 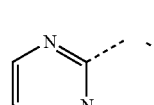 | 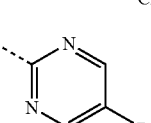 | $t_R$ = 5.28 min<br>$[M + H]^+$: 604.11<br>$[M - H]^-$: 602.42 |
| 14 | 3 | 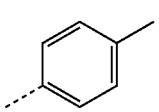 | 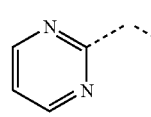 | 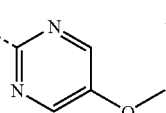 | $t_R$ = 5.33 min<br>$[M + H]^+$: 647.96<br>$[M - H + 2]^-$: 647.52 |
| 15 | 3 | 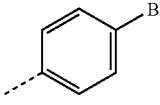 |  | 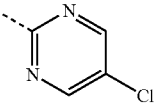 | $t_R$ = 4.97 min<br>$[M + H]^+$: 600.19<br>$[M - H]^-$: 598.28 |
| 16 | 4 | 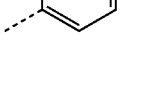 | H | 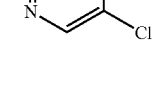 | $t_R$ = 5.51 min<br>$[M + H]^+$: 589.97<br>$[M - H]^-$: 587.47 |

TABLE 1-continued

| Ex. No | Ref. Ex. No | R¹ | R² | R³ | LC-MS |
|---|---|---|---|---|---|
| 17 | 4 | 4-Br-phenyl | H | 5-Br-pyrimidin-2-yl | $t_R$ = 5.56 min<br>[M + 2 + H]⁺: 636.23<br>[M − H]⁻: 632.12 |
| 18 | 4 | 4-Br-phenyl | H | 5-OMe-pyrimidin-2-yl | $t_R$ = 5.18 min<br>[M + H + 2]⁺: 587.88<br>[M − H]⁻: 583.91 |
| 19 | 5 | 3,4-dimethylphenyl | H | 5-Br-pyrimidin-2-yl | $t_R$ = 5.59 min<br>[M + H]⁺: 584.10<br>[M − H + 2]⁻: 583.54 |
| 20 | 5 | 3,4-dimethylphenyl | H | 5-OMe-pyrimidin-2-yl | $t_R$ = 5.24 min<br>[M + H]⁺: 536.32<br>[M − H]⁻: 534.40 |
| 21 | 6 | 3,5-dimethylphenyl | H | 5-Br-pyrimidin-2-yl | $t_R$ = 5.55 min<br>[M + H]⁺: 584.18<br>[M − H]⁻: 582.12 |
| 22 | 6 | 3,5-dimethylphenyl | H | 5-SMe-pyrimidin-2-yl | $t_R$ = 5.46 min<br>[M + H]⁺: 552.03<br>[M − H]⁻: 550.15 |
| 23 | 7 | 2,3-dimethoxyphenyl | pyridin-4-yl | pyrimidin-2-yl | $t_R$ = 4.47 min<br>[M + H]⁺: 600.95<br>[M − H]⁻: 598.84 |
| 24 | 7 | 2,3-dimethoxyphenyl | pyridin-4-yl | 5-Cl-pyrimidin-2-yl | $t_R$ = 4.97 min<br>[M + H]⁺: 635.16<br>[M − H]⁻: 632.99 |

TABLE 1-continued
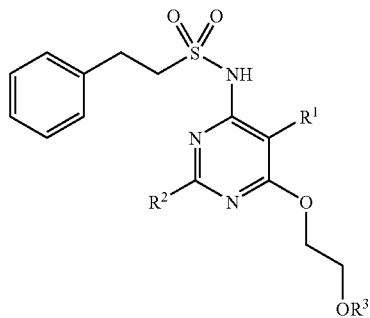
| Ex. No | Ref. Ex. No | R¹ | R² | R³ | LC-MS |
|---|---|---|---|---|---|
| 25 | 7 | 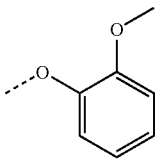 | 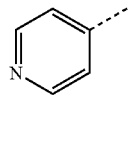 | 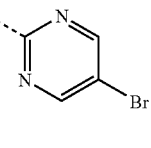 | $t_R$ = 5.02 min<br>$[M + H]^+$: 679.17<br>$[M - H]^-$: — |
| 26 | 7 | 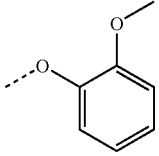 | 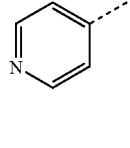 | 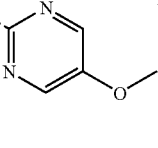 | $t_R$ = 4.68 min<br>$[M + H]^+$: 631.30<br>$[M - H]^-$: 629.22 |
| 27 | 8 | 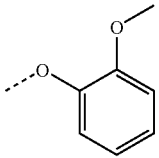 | 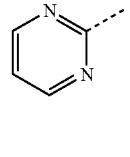 | 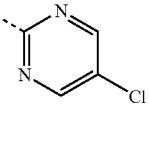 | $t_R$ = 4.90 min<br>$[M + H]^+$: 636.17<br>$[M - H]^-$: 634.43 |
| 28 | 8 | 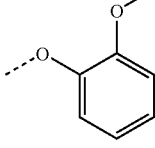 | 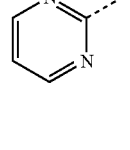 | 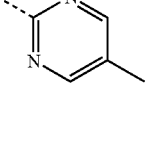 | $t_R$ = 4.73 min<br>$[M + H]^+$: 614.10<br>$[M - H]^-$: 612.15 |
| 29 | 8 | 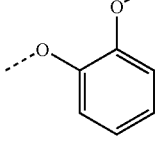 | 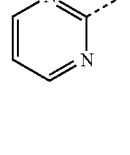 | 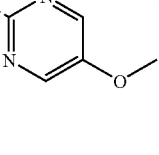 | $t_R$ = 4.68 min<br>$[M + H]^+$: 632.33<br>$[M - H]^-$: 630.00 |
| 30 | 8 | 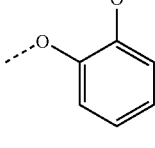 | 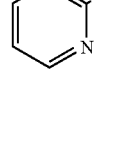 | 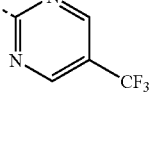 | $t_R$ = 5.08 min<br>$[M + H]^+$: 670.19<br>$[M - H]^-$: 668.34 |
| 31 | 8 | 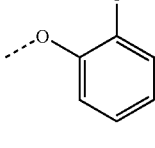 | 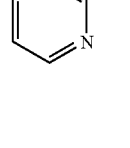 | 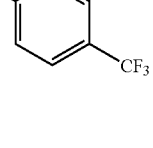 | $t_R$ = 5.42 min<br>$[M + H]^+$: 669.05<br>$[M - H]^-$: 666.80 |

TABLE 1-continued

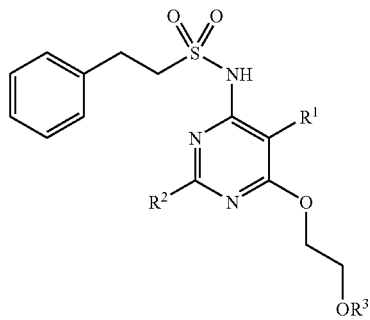

| Ex. No | Ref. Ex. No | R¹ | R² | R³ | LC-MS |
|---|---|---|---|---|---|
| 32 | 9 | 2-methoxyphenoxy | pyrazinyl | pyrimidin-2-yl | $t_R$ = 4.70 min<br>$[M + H]^+$: 602.25<br>$[M - H]^-$: 600.18 |
| 33 | 9 | 2-methoxyphenoxy | pyrazinyl | 5-bromopyrimidin-2-yl | $t_R$ = 5.19 min<br>$[M + H + 2]^+$: 681.96<br>$[M - H]^-$: 678.21 |
| 34 | 9 | 2-methoxyphenoxy | pyrazinyl | 5-methoxypyrimidin-2-yl | $t_R$ = 4.88 min<br>$[M + H]^+$: 632.24<br>$[M - H]^-$: 630.35 |
| 35 | 9 | 2-methoxyphenoxy | pyrazinyl | 5-methylthiopyrimidin-2-yl | $t_R$ = 5.11 min<br>$[M + H]^+$: 648.57<br>$[M - H]^-$: 646.11 |
| 36 | 10 | 2-methoxyphenoxy | morpholinyl | pyrimidin-2-yl | $t_R$ = 5.13 min<br>$[M + H]^+$: 609.31<br>$[M - H]^-$: 607.25 |
| 37 | 10 | 2-methoxyphenoxy | morpholinyl | 5-bromopyrimidin-2-yl | $t_R$ = 5.67 min<br>$[M + H]^+$: 686.92<br>$[M - H]^-$: 685.02 |
| 38 | 10 | 2-methoxyphenoxy | morpholinyl | 5-methoxypyrimidin-2-yl | $t_R$ = 5.30 min<br>$[M + H]^+$: 639.30<br>$[M - H]^-$: 637.13 |

TABLE 1-continued

[Core structure: N-(pyrimidin-4-yl)-2-phenylethanesulfonamide with R¹ at 5-position, R² at 2-position, and 6-O-CH₂CH₂-OR³]

| Ex. No | Ref. Ex. No | R¹ | R² | R³ | LC-MS |
|---|---|---|---|---|---|
| 39 | 10 | 2-methoxyphenoxy | morpholin-4-yl | 5-(methylthio)pyrimidin-2-yl | $t_R$ = 5.51 min; [M + H]⁺: 654.92; [M − H]⁻: 653.08 |
| 40 | 11 | 2-methoxyphenoxy | H | pyrimidin-2-yl | $t_R$ = 4.84 min; [M + Na]⁺: 524.32; [M − H]⁻: 522.00 |
| 41 | 11 | 2-methoxyphenoxy | H | 5-bromopyrimidin-2-yl | $t_R$ = 5.38 min; [M + H]⁺: 601.95; [M − H]⁻: 600.33 |
| 42 | 11 | 2-methoxyphenoxy | H | 5-methoxypyrimidin-2-yl | $t_R$ = 5.01 min; [M + H]⁺: 554.14; [M − H]⁻: 552.03 |
| 43 | 11 | 2-methoxyphenoxy | H | 5-(trifluoromethyl)pyridin-2-yl | $t_R$ = 5.75 min; [M + H]⁺: 591.44; [M − H]⁻: 588.99 |
| 44 | 12 | 3-(morpholin-4-yl)phenoxy | H | 5-bromopyrimidin-2-yl | $t_R$ = 5.52 min; [M + H]⁺: 687.24; [M − H]⁻: 685.44 |
| 45 | 12 | 3-(morpholin-4-yl)phenoxy | H | 5-methoxypyrimidin-2-yl | $t_R$ = 5.18 min; [M + H]⁺: 639.32; [M − H]⁻: 637.14 |
| 46 | 13 | 3-methoxyphenoxy | H | 5-bromopyrimidin-2-yl | $t_R$ = 5.25 min; [M + H]⁺: 602.00; [M − H]⁻: 599.99 |

TABLE 1-continued
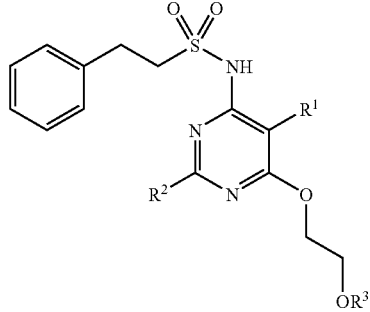
| Ex. No | Ref. Ex. No | R¹ | R² | R³ | LC-MS |
|---|---|---|---|---|---|
| 47 | 13 | 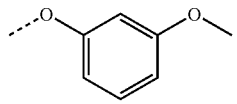 | H | 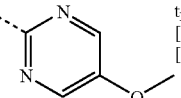 | $t_R$ = 4.89 min<br>$[M + H]^+$: 553.98<br>$[M - H]^-$: 551.97 |
TABLE 2
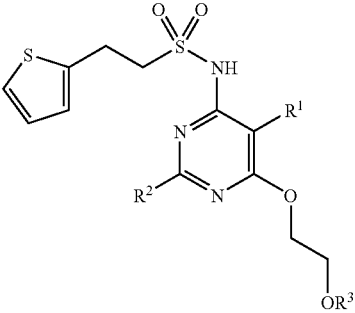
| Ex. No | Ref. Ex. No | R¹ | R² | R³ | LC-MS |
|---|---|---|---|---|---|
| 48 | 14 | 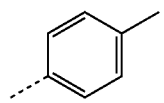 | H | 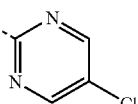 | $t_R$ = 5.24 min<br>$[M + H]^+$: 532.13<br>$[M - H]^-$: 530.35 |
| 49 | 14 | 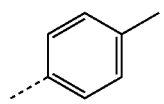 | H | 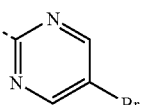 | $t_R$ = 5.31 min<br>$[M + H]^+$: 576.07<br>$[M - H]^-$: 574.19 |
| 50 | 14 | 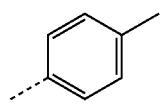 | H | 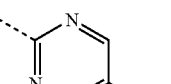 | $t_R$ = 4.95 min<br>$[M + H]^+$: 528.17<br>$[M - H]^-$: 526.12 |
| 51 | 15 | 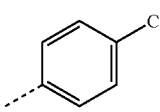 | H | 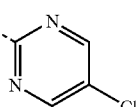 | $t_R$ = 5.28 min<br>$[M + H]^+$: 552.39<br>$[M - H]^-$: 550.27 |
| 52 | 15 | 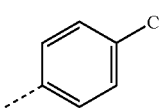 | H | 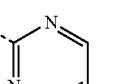 | $t_R$ = 5.33 min<br>$[M + H + 2]^+$: 598.29<br>$[M - H]^-$: 595.43 |

TABLE 2-continued

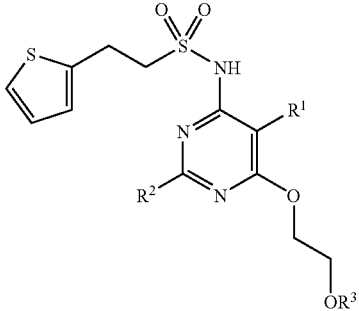

| Ex. No | Ref. Ex. No | R¹ | R² | R³ | LC-MS |
|---|---|---|---|---|---|
| 53 | 15 | 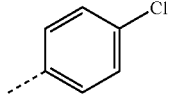 4-Cl-phenyl | H | 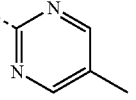 5-methyl-pyrimidin-2-yl | $t_R$ = 5.07 min<br>[M + H]⁺: 532.29<br>[M − H]⁻: 529.95 |
| 54 | 15 | 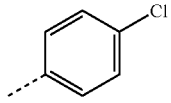 4-Cl-phenyl | H | 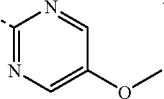 5-methoxy-pyrimidin-2-yl | $t_R$ = 4.99 min<br>[M + H]⁺: 547.89<br>[M − H]⁻: 545.91 |
| 55 | 16 | 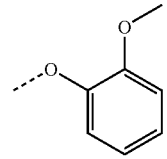 2-methoxy-phenoxy | 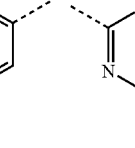 pyridin-4-yl | 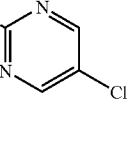 5-chloro-pyrimidin-2-yl | $t_R$ = 5.07 min<br>[M + H]⁺: 641.16<br>[M − H]⁻: 638.75 |
| 56 | 16 | 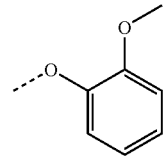 2-methoxy-phenoxy | 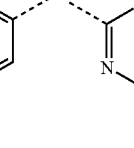 pyridin-4-yl |  5-bromo-pyrimidin-2-yl | $t_R$ = 4.96 min<br>[M + H]⁺: 685.12<br>[M − H]⁻: 683.33 |
| 57 | 16 | 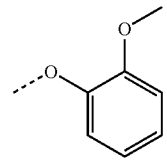 2-methoxy-phenoxy | 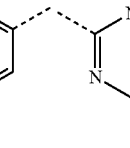 pyridin-4-yl | 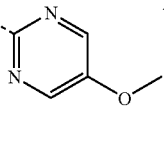 5-methoxy-pyrimidin-2-yl | $t_R$ = 4.62 min<br>[M + H]⁺: 637.18<br>[M − H]⁻: 635.04 |
| 58 | 17 | 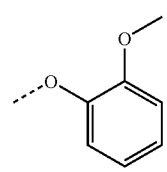 2-methoxy-phenoxy | 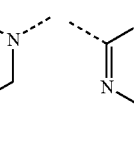 morpholin-4-yl | 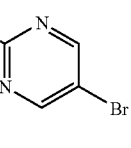 5-bromo-pyrimidin-2-yl | $t_R$ = 5.56 min<br>[M + H]⁺: 693.12<br>[M − H]⁻: 691.31 |
| 59 | 17 | 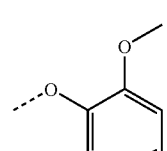 2-methoxy-phenoxy | 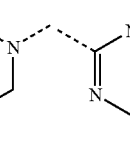 morpholin-4-yl | 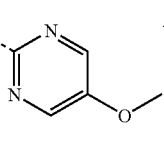 5-methoxy-pyrimidin-2-yl | $t_R$ = 5.21 min<br>[M + H]⁺: 645.35<br>[M − H]⁻: 643.48 |

TABLE 3
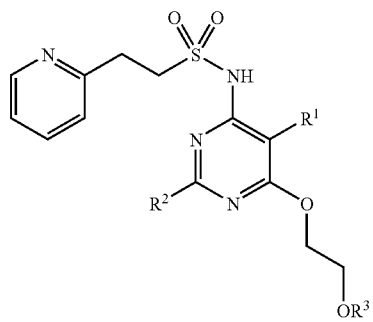
| Ex. No | Ref. Ex. No | R¹ | R² | R³ | LC-MS |
|---|---|---|---|---|---|
| 60 | 18 | 2-methoxyphenoxy | 4-pyridyl | 2-pyrimidinyl | $t_R$ = 3.56 min<br>[M + H]⁺: 602.40<br>[M − H]⁻: 600.14 |
| 61 | 18 | 2-methoxyphenoxy | 4-pyridyl | 5-bromo-2-pyrimidinyl | $t_R$ = 4.14 min<br>[M + H + 2]⁺: 682.26<br>[M − H]⁻: 678.23 |
TABLE 4
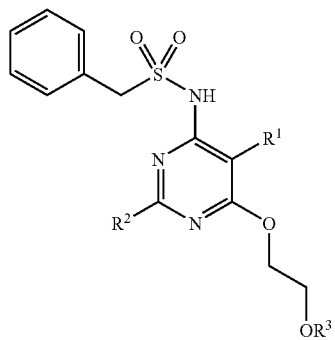
| Ex. No | Ref. Ex. No | R¹ | R² | R³ | LC-MS |
|---|---|---|---|---|---|
| 62 | 19 | 2-methoxyphenoxy | 4-pyridyl | 2-pyrimidinyl | $t_R$ = 4.46 min<br>[M + H]⁺: 587.43<br>[M − H]⁻: 585.40 |
| 63 | 19 | 2-methoxyphenoxy | 4-pyridyl | 5-bromo-2-pyrimidinyl | $t_R$ = 5.00 min<br>[M + H + 2]⁺: 667.12<br>[M − H + 2]⁻: 665.47 |

TABLE 4-continued
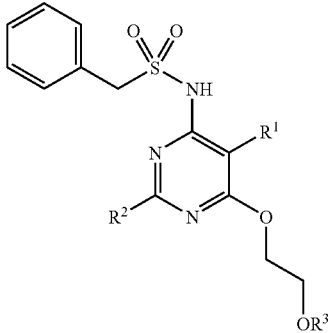
| Ex. No | Ref. Ex. No | R¹ | R² | R³ | LC-MS |
|---|---|---|---|---|---|
| 64 | 19 | 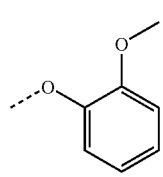 | 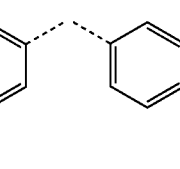 | 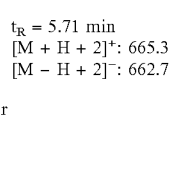 | $t_R$ = 5.71 min<br>$[M + H + 2]^+$: 665.39<br>$[M - H + 2]^-$: 662.71 |
| 65 | 20 | 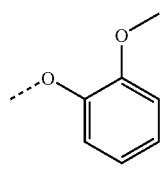 | 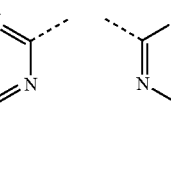 | 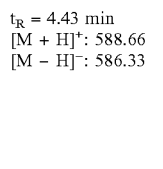 | $t_R$ = 4.43 min<br>$[M + H]^+$: 588.66<br>$[M - H]^-$: 586.33 |
| 66 | 20 | 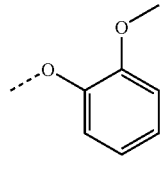 | 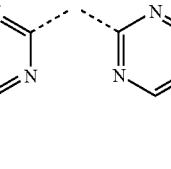 | 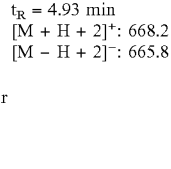 | $t_R$ = 4.93 min<br>$[M + H + 2]^+$: 668.21<br>$[M - H + 2]^-$: 665.81 |
| 67 | 20 | 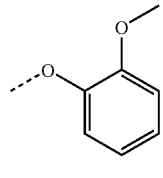 | 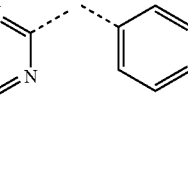 | 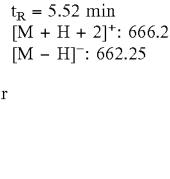 | $t_R$ = 5.52 min<br>$[M + H + 2]^+$: 666.29<br>$[M - H]^-$: 662.25 |
| 68 | 21 | 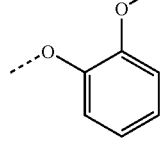 | 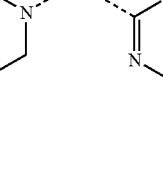 | 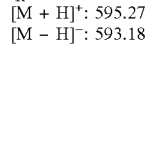 | $t_R$ = 5.01 min<br>$[M + H]^+$: 595.27<br>$[M - H]^-$: 593.18 |
| 69 | 21 | 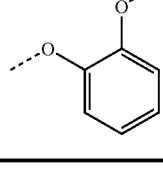 | 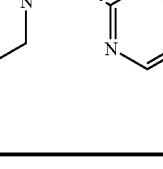 | 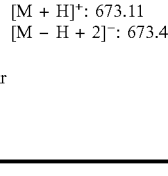 | $t_R$ = 5.46 min<br>$[M + H]^+$: 673.11<br>$[M - H + 2]^-$: 673.42 |

TABLE 5
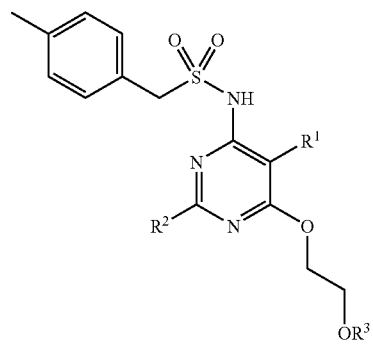
| Ex. No | Ref. Ex. No | R¹ | R² | R³ | LC-MS |
|---|---|---|---|---|---|
| 70 | 22 | 2-methoxyphenoxy | pyridin-4-yl | pyrimidin-2-yl | $t_R$ = 4.58 min<br>$[M + H]^+$: 601.39<br>$[M - H]^-$: 599.12 |
| 71 | 22 | 2-methoxyphenoxy | pyridin-4-yl | 5-bromopyrimidin-2-yl | $t_R$ = 5.28 min<br>$[M + H + 2]^+$: 681.24<br>$[M - H]^-$: 677.00 |
| 72 | 23 | 2-methoxyphenoxy | pyrazin-2-yl | pyrimidin-2-yl | $t_R$ = 4.76 min<br>$[M + H]^+$: 602.20<br>$[M - H]^-$: 600.18 |
| 73 | 23 | 2-methoxyphenoxy | pyrazin-2-yl | 5-bromopyrimidin-2-yl | $t_R$ = 5.24 min<br>$[M + H]^+$: 680.13<br>$[M - H]^-$: 678.14 |

TABLE 6
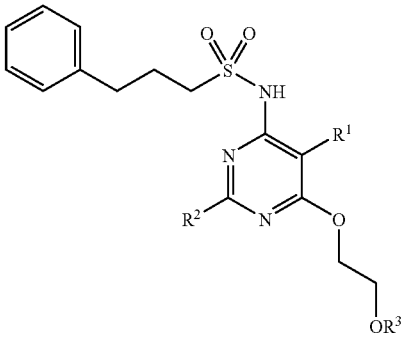
| Ex. No | Ref. Ex. No | R¹ | R² | R³ | LC-MS |
|---|---|---|---|---|---|
| 74 | 24 | 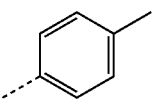 | H | 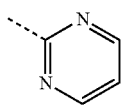 | t_R = 5.13 min<br>[M + H]⁺: 506.25<br>[M − H]⁻: 504.26 |
| 75 | 24 | 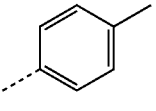 | H | 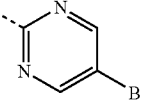 | t_R = 5.62 min<br>[M + H + 2]⁺: 586.33<br>[M − H]⁻: 582.11 |
| 76 | 25 | 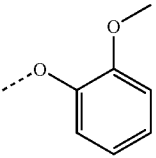 | 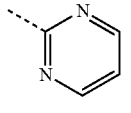 | 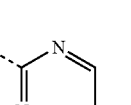 | t_R = 4.56 min<br>[M + H]⁺: 615.53<br>[M − H]⁻: 613.40 |
| 77 | 25 | 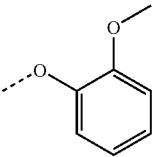 | 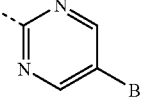 | 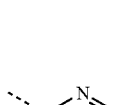 | t_R = 5.09 min<br>[M + H]⁺: 693.22<br>[M − H]⁻: 691.07 |
| 78 | 26 | 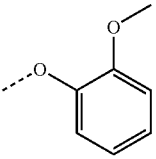 | 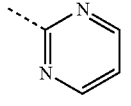 | 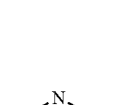 | t_R = 4.58 min<br>[M + H]⁺: 616.54<br>[M − H]⁻: 614.29 |
| 79 | 26 | 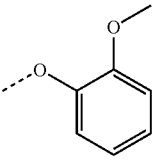 | 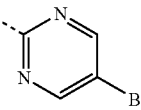 | 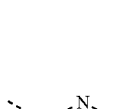 | t_R = 5.09 min<br>[M + H]⁺: 694.42<br>[M − H]⁻: 692.21 |
| 80 | 27 | 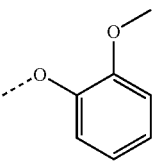 | 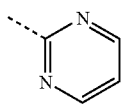 |  | t_R = 5.20 min<br>[M + H]⁺: 623.37<br>[M − H]⁻: 621.19 |

TABLE 6-continued
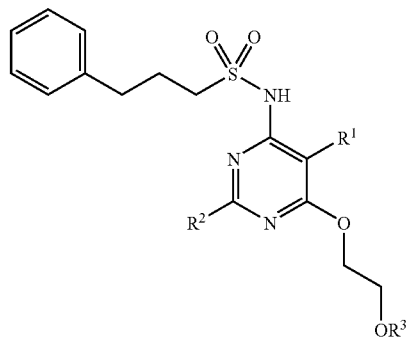
| Ex. No | Ref. Ex. No | R¹ | R² | R³ | LC-MS |
|---|---|---|---|---|---|
| 81 | 27 | ![methoxyphenyl] | ![morpholinyl-pyrimidinyl] | ![bromopyrimidinyl] | $t_R$ = 5.66 min<br>$[M + H + 2]^+$: 703.51<br>$[M - H + 2]^-$: 701.52 |
TABLE 7
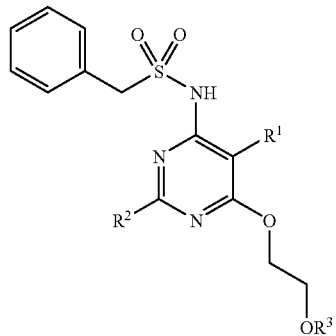
| Ex. No | Ref. Ex. No | R¹ | R² | R³ | LC-MS |
|---|---|---|---|---|---|
| 82 | 28 | ![methoxyphenyl] | ![pyrimidinyl] | ![pyrimidinyl] | $t_R$ = 4.55 min<br>$[M + H]^+$: 602.43<br>$[M - H]^-$: 600.26 |
| 83 | 28 | ![methoxyphenyl] | ![pyrimidinyl] | ![CF₃-pyridinyl] | $t_R$ = 5.59 min<br>$[M + H]^+$: 669.49<br>$[M - H]^-$: 667.40 |

TABLE 8

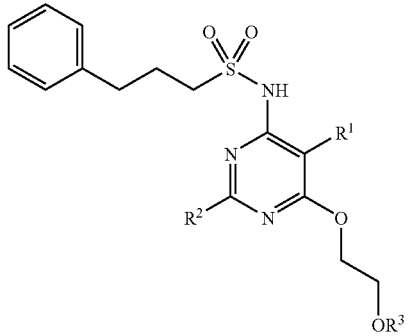

| Ex. No | Ref. Ex. No | R¹ | R² | R³ | LC-MS |
|---|---|---|---|---|---|
| 84 | 29 | (4-methylphenyl) | H | (5-bromopyrimidin-2-yl) | $t_R$ = 5.71 min<br>$[M + H + 2]^+$: 600.18<br>$[M - H]^-$: 596.05 |
| 85 | 29 | (4-methylphenyl) | H | (5-bromopyridin-2-yl) | $t_R$ = 6.21 min<br>$[M + H + 2]^+$: 598.96<br>$[M - H]^-$: 594.67 |
| 86 | 29 | (4-methylphenyl) | H | (5-trifluoromethylpyridin-2-yl) | $t_R$ = 6.16 min<br>$[M + H]^+$: 587.19<br>$[M - H]^-$: 584.74 |

The invention claimed is:

1. A compound of the formula I

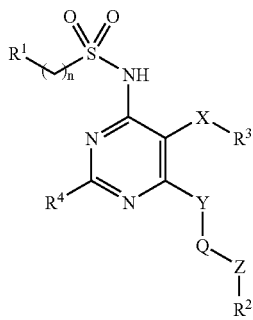

Formula I wherein

R¹ and R² represent aryl or heteroaryl;

R³ represents phenyl; mono-, di- or tri-substituted phenyl substituted with substituents selected from the group consisting of lower alkyl, lower alkenyl, lower alkynyl, phenyl, lower alkoxy, amino, lower alkylamino, amino-lower alkyl, trifluoromethyl, trifluoromethoxy, halogen, lower alkylthio, hydroxy, hydroxy-lower alkyl, cyano, carboxyl, lower alkanoyl and formyl; benzofuranyl; or heteroaryl;

R⁴ represents hydrogen; halogen; trifluoromethyl; lower alkyl; lower alkyl-amino; lower alkoxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl- lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; or cycloalkyl-sulfinyl;

X represents oxygen; sulfur; NH; CH₂ or a bond;

Y represents oxygen; sulfur or —NH—;

Z represents oxygen; sulfur, —NH— or a bond;

Q represents —(CH₂)$_k$—; —(CH₂)$_m$—C≡C—(CH₂)$_p$—, in case p represents 0 (zero), Z represents a bond; or —CH₂-cyclopropylen-CH₂—;

k represents the numbers 2, 3, 4, 5, or 6;

m represents the numbers 1, 2, or 3;

p represents the numbers 0, 1, 2 or 3;

n represents the numbers 1, 2, or 3;

or pure diastereomers, mixtures of diastereomers, diastereomeric racemates, mixtures of diastereomeric racemates, the meso-forms or pharmaceutically acceptable salts thereof.

2. The compound of claim 1, wherein $R^1$, $R^2$, $R^4$, Q, Y, Z and n are as defined in claim 1, X, represents oxygen and $R^3$ represents phenyl or mono-substituted phenyl substituted with halogen, lower alkyl, lower alkenyl, lower alkoxy, amino, lower alkyl-amino, lower alkyl-thio, hydroxy, hydroxymethyl or lower alkanoyl;

or pharmaceutically acceptable salts thereof.

3. The compound of claim 1, wherein $R^1$, $R^2$, $R^4$, Q, and n are as defined in claim 1, X, Y and Z represent oxygen and $R^3$ represents phenyl or mono-substituted phenyl substituted with halogen, lower alkyl, lower alkenyl, lower alkoxy, amino, lower alkyl-amino, lower alkyl-thio, hydroxy, hydroxymethyl or lower alkanoyl;

or pharmaceutically acceptable salts thereof.

4. The compound of claim 1, wherein $R^1$, $R^2$, $R^4$, and n are as defined in claim 1, X, Y and Z represent oxygen, Q represents —$(CH_2)_k$— with k=2 or 3 and $R^3$ represents phenyl or mono-substituted phenyl substituted with halogen, lower alkyl, lower alkenyl, lower alkoxy, amino, lower alkyl-amino, lower alkyl-thio, hydroxy, hydroxymethyl or lower alkanoyl;

or pharmaceutically acceptable salts thereof.

5. The compound of claim 1, wherein $R^1$, $R^4$, and n are as defined in claim 1, X, Y and Z represent oxygen, Q represents —$(CH_2)_k$— with k=2 or 3, $R^2$ represents heteroaryl and $R^3$ represents phenyl or mono-substituted phenyl substituted with halogen, lower alkyl, lower alkenyl, lower alkoxy, amino, lower alkyl-amino, lower alkyl-thio, hydroxy, hydroxymethyl or lower alkanoyl;

or pharmaceutically acceptable salts thereof.

6. The compound of claim 1, wherein $R^1$, $R^4$, and n are as defined in claim 1, X, Y and Z represent oxygen, Q represents —$(CH_2)_2$—, $R^2$ represents heteroaryl, $R^3$ represents phenyl or mono-substituted phenyl substituted with halogen, lower alkyl, lower alkenyl, methoxy, amino, lower alkyl-amino, lower alkyl-thio, hydroxy, hydroxymethyl or lower alkanoyl;

or pharmaceutically acceptable salts thereof.

7. A compound of formula II

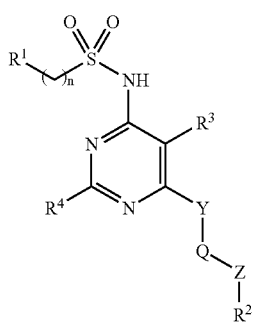

Formula II wherein $R^1$, $R^2$, $R^3$, $R^4$, Y, Q, Z and n are as defined in claim 1 above, or pharmaceutically acceptable salts thereof.

8. A compound of formula III

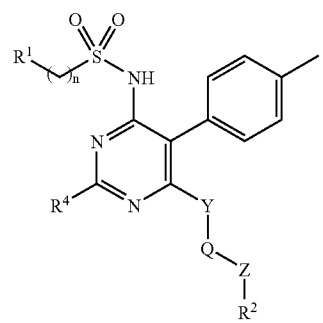

Formula III wherein $R^1$, $R^2$, $R^4$, Y, Q, Z and n are as defined in claim 1 above, or pharmaceutically acceptable salts thereof.

9. A compound of formula IV

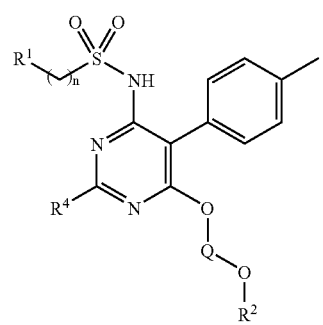

Formula IV wherein $R^1$, $R^2$, $R^4$, Q and n are as defined in claim 1 above, or pharmaceutically acceptable salts thereof.

10. A compound of formula V

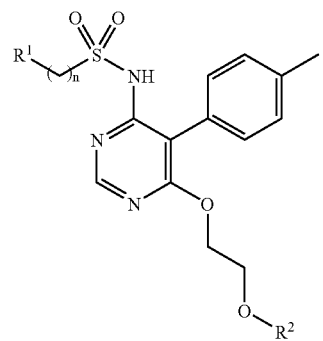

Formula V wherein $R^1$, $R^2$ and n are as defined in claim 1 above, or pharmaceutically acceptable salts thereof.

11. The compound of claim 10, wherein $R^2$ in formula V represents heteroaryl or pharmaceutically acceptable salts thereof.

12. The compound of claim 1 wherein said compound is selected from the group consisting of:

2-Phenyl-ethanesulfonic acid {6-[2-(5-bromo-pyrimidin-2-yloxy)-ethoxy]-5-p-tolyl -pyrimidin-4-yl}-amide, 2-Phenyl-ethanesulfonic acid {6-[2-(5-bromo-pyrimidin-2-yloxy)-ethoxy]-5-p-tolyl-[2,2']bipyrimidinyl-4-yl}-amide,
2-Phenyl-ethanesulfonic acid {5-(2-methoxy-phenoxy)-6-[2-(pyrimidin-2-yloxy)-ethoxy]-[2,2']bipyrimidinyl-4-yl}-amide,
2-Phenyl-ethanesulfonic acid {5-(2-methoxy-phenoxy)-6-[2-(5-methoxy-pyrimidin-2-yloxy)-ethoxy]-[2,2']bipyrimidinyl-4-yl}-amide,
2-Thiophen-2-yl-ethanesulfonic acid [6-[2-(5-bromo-pyrimidin-2-yloxy)-ethoxy]-5-(4-chloro-phenyl)-pyrimidin-4-yl]-amide,
2-Thiophen-2-yl-ethanesulfonic acid {5-(4-chloro-phenyl)-6-[2-(5-methoxy-pyrimidin-2-yloxy)-ethoxy]-pyrimidin-4-yl}-amide,
2-Pyridin-2-yl-ethanesulfonic acid [6-[2-(5-bromo-pyrimidin-2-yloxy)-ethoxy]-5-(2-methoxy-phenoxy)-2-pyridin-4-yl-pyrimidin-4-yl]-amide, and pharmaceutically acceptable salts thereof.

13. A pharmaceutical composition comprising one or more of the compounds of any one of claims 1, 7, 8, 9 and 10 and a pharmaceutically acceptable carrier.

14. A process for preparing a pharmaceutical composition, comprising mixing one or more compounds of any one of claims 1, 7, 8, 9 and 10 with a pharmaceutically acceptable carrier.

\* \* \* \* \*